United States Patent [19]
Young et al.

[11] Patent Number: 5,960,443
[45] Date of Patent: Sep. 28, 1999

[54] QUANTITATIVE VISUAL SYSTEM FOR COMPARING PARAMETERS WHICH CHARACTERIZE MULTIPLE COMPLEX ENTITIES

[76] Inventors: David E. Young, 16 Couching Street, Watlington, Oxfordshire OX9 5QQ, United Kingdom; DeWitt J. Lowell, 6622 - 138th Pl. SW., Edmonds, Wash. 98026

[21] Appl. No.: 08/995,576

[22] Filed: Oct. 28, 1997

Related U.S. Application Data

[60] Provisional application No. 60/053,791, Jul. 25, 1997.

[51] Int. Cl.$^6$ ............................. G06F 17/30; G06K 9/00
[52] U.S. Cl. .......................... 707/104; 707/100; 623/11; 435/4
[58] Field of Search .................................. 707/100, 200, 707/104; 364/222.81, 225, 227.3, 286; 395/500; 606/1; 600/476; 250/339.08; 514/302; 435/4; 623/11

[56] References Cited

U.S. PATENT DOCUMENTS

| | | | |
|---|---|---|---|
| 4,570,638 | 2/1986 | Stoddart et al. | 600/476 |
| 4,628,928 | 12/1986 | Lowell | 606/1 |
| 5,010,478 | 4/1991 | Deran | 707/100 |
| 5,193,182 | 3/1993 | Bachman et al. | 707/100 |
| 5,539,207 | 7/1996 | Wong | 250/339.08 |

*Primary Examiner*—Paul R. Lintz
*Assistant Examiner*—Sanjiv Shah
*Attorney, Agent, or Firm*—Tilton, Fallon, Lungmus & Chestnut

[57] ABSTRACT

A system for comparing two complex entities, particularly appropriate for assisting in matching recipients with potential organ transplant donors or prostheses, utilizes a set of data corresponding to multiple diverse parameters representing a first complex entity, graphically represented on a helical structure having a discrete primary zone for each parameter and a series of secondary zones within each primary zone to establish scale means for quantitative representation of the data. The data is represented in a visual manner by means of shading in the secondary zones, with the shading increasing in hue and density with increasing distance of the secondary zones from the longitudinal axis of the helical structure, and terminating at a quantitative value for each parameter. Other sets of data corresponding to other complex entities are similarly represented on additional helical structures, and the helixes, or sections thereof, are superimposed on one another to determine the suitability of a match, with differences in values for each parameter being readily visible to an observer by looking at the differences in termination of the shaded regions.

38 Claims, 10 Drawing Sheets

QUANTITATIVE VISUAL SYSTEM FOR COMPARING PARAMETERS WHICH CHARACTERIZE MULTIPLE COMPLEX ENTITIES

REFERENCE TO RELATED APPLICATIONS

This application is entitled to the benefit of the filing date of U.S. Provisional Application Ser. No. 60/053,791, filed Jul. 25, 1997.

BACKGROUND

1. Field of the Invention

The present invention relates generally to comparing sets of complex data, and in particular to a system for making integrated, visual comparisons between characteristics of complex entities represented by data subsets.

An example within this general field and one to which the present invention is particularly applicable, is surgical transplantation. This includes prosthetic implants, reimplantation of expanded autograft tissues and most particularly and valuably, to human allograft transplantation into humans.

Though not limited to this field, the invention provides, in this context, a novel, structurally based, practical system for matching potential recipient parameters to a donor organ or prosthesis and means for controlling and communicating inventory data on donor organs and prostheses. This enables a provider of prostheses or organs to provide significant assistance to the surgical and scientific team in the selection and decision making process. The invention is further concerned with the field of means for enhancing the quality of clinical judgment brought to bear on individual transplant and implant cases by virtue of the manner and form in which the information is presented. The present invention has significant utility for any group of suppliers and users which face similarly complex sets of data parameters.

2. Description of Related Art

For the lay person and indeed, the scientific and medical communities, matching a requirement to an available product or service may be adequately addressed via the well-known device of a catalog of inventory. Typically, this will involve a general specification of the item, with or without an illustration and followed by a simple numerical or alphanumerical code, which enables an appropriate selection to be made. Such simple systems work well for the vast majority of items which society needs to transfer between suppliers and users because users can typically determine whether a particular item meets their needs by reviewing the general specification of the item and the illustration, if provided, in the catalog. If users are still unsure as to the adequacy of a particular item for their needs, there are generally personnel available to answer questions.

In cases of custom requirements, the additional use of mechanical or electrical drawings, bills of materials, specifications and other forms of extended data, are tools that are well known and understood. In most situations they serve the parties adequately.

All of these listing tools typically need to be used in sequence or side-by-side in a disparate and non-integrated manner. There is no system known to the present inventors which unifies all important data subsets relating to very complex products and which allows simultaneous quantitative and qualitative judgments to be derived from it.

In the rapidly developing field of organ transplantation and to a lesser extent in the field of prosthetic implantation, however, there are many more points of difference in the relationship between the supplying entity and the potential recipient than are encountered in the supplier-vendor relationships of normal commerce. These differences, the complexity and number of matching parameters and the life-critical nature of the transaction, render simple inventory systems at best, inadequate, and at worst, unworkable. In the absence of advances in the state of the art, this problem will worsen as xenotransplantation becomes accepted and commonplace.

With organ transplantation, in particular, most requirements relate to situations where the potential recipient has a relatively short or very short time in which to receive a replacement, if he or she is to survive. This is because failure of a major organ is usually accompanied by deterioration of other systems, leading to a generalized metabolic catastrophe. An article in FORTUNE magazine published Nov. 25, 1996, stated that "About 18,000 human organs are transplanted annually in the U.S., while an estimated 100,000 Americans die waiting for a spare heart, liver, kidney, or other organ." The serious shortfall in supply is one of the significant driving forces behind the major upsurge in interest in xenotransplantation and in particular, projects which are currently being undertaken by a number of companies to develop genetically modified pigs as a potential future source of organs. For the first time, the possibility arises of generating an adequate number of organs with physical characteristics which may be matched better than is often the case with human allografts, where the emphasis has necessarily been on matching by tissue-typing alone.

This increases the need for inventory systems which will be able to deal with many additional important parameters. However, even the currently used tissue histocompatibility parameters are presented as line-by-line data, which encourages item-by-item comparisons and value judgments which are, of necessity, fragmented. These inventors are not aware of any transplant team nor donor organ supplying organization which uses or has proposed using, any system which offers a basis for integrating transplant parameters into a visual presentation which would facilitate an integrated decision making process.

Orthopedic surgeons are one group of medical specialists who carry out large numbers of implantation procedures. They have complex needs in respect of such procedures but they have also been better provided for than most groups of specialists with means for making assisted judgments. For instance, radiography of the calcified skeleton has allowed accurate measurements to be made on bones and joint spaces for many decades. Additionally, in the example of total hip-joint replacement, line-art transparent overlays of a series of standard sizes of a preferred prosthesis may be placed over appropriate x-ray views of the subject joint and adjacent bones until the right size is identified. By these means, a surgeon is able to predict, within reasonable limits, what will be needed, from inventory, at the time of surgery and normally will be able to comfortably predict the outcome.

Even though the range of metal and plastic conventional prosthetic implants now in common use is very wide, such implants do not, even at their most complicated, ever approach the complexity of a human or animal organ. The prediction of intra-operative requirements and outcomes in prosthetic replacements of soft tissues has been considerably assisted by the advent of techniques such a magnetic resonance imaging (MRI) and computerized axial tomography scanning (CAT), though these techniques are complex and relatively costly. However, the only so-called advance in the selection, supply and inventory process, for any type of conventual prosthesis has been the advent of Electronic Data Transfer (EDT). In such systems, manufacturers provide on-line, line-by-line inventory data to their purchasing client groups who may place orders for their requirements within the system. In fact, this is just an on-line catalog listing and order processing facility and is not well-suited to highly complex, urgent situations.

Meanwhile, tissue regeneration techniques are improving rapidly. For instance, human tissues can now be removed from a subject and grown outside the body for reimplantation later. Techniques are being developed which will use both organic and inorganic materials, as scaffolds, to support the growth of such explanted tissues. These scaffold materials will have varying antigenic potential and it is known, in addition, that processing human tissue, extracorporeally, can lead to an antigenic profile which may diverge from that of the original sample. As reimplantation of expanded autogenous tissues, with or without scaffolds, gains acceptance, the old and accepted definitions of prosthetic replacement are becoming less adequate.

Sophisticated surgical opportunities, with tissue-augmented prostheses, will increase demands on surgical teams, who will require better tools and more varied data to prospectively evaluate the chances of a successful outcome. New means for matching the complex needs of the user to the supplier are urgently required.

This dilemma may be illustrated by considering the well documented phenomena of hyperacute, acute and long term rejection. While it is likely that progress will be made in these areas, it is inevitable that this progress will be accompanied by a proliferation of data species which will need to be collected and considered. This need will apply not only to potential recipients but will also need to be 'attached', maintained and supplied in respect of replacement organs and tissue augmented prostheses.

Transplant teams comprise individuals, from varying technical fields, who have great experience, as well as practical and technical skills. They also have human quality of judgment, the subtlety of which is refined by repeated exposure to demanding situations. There is and will be an increasing need for improved data presentation which will allow that subtlety of judgment to be exercised, enhanced and refined.

SUMMARY OF THE PRESENT INVENTION

The present invention provides a system which includes structurally based, visual means which may be employed in managing large numbers of data subsets within varied data species, used to characterize multiple complex entities and for making integrated, visual, comparisons between such entities on a quantitative, as well as qualitative basis. The object of the invention is to facilitate and increase the speed with which such data may be exchanged between a supplier of complex entities and a user whose needs require close matching of a product to its application. Further, the visual, quantitative basis of the instant system provides means for enhancing the quality and speed of decisions reached by those who use the system in situations where time is of the essence.

In an exemplary application, the data species include, among others, multiple histocompatibility factors, anatomical, morphological and functional markers for a human or animal which is intended to receive a transplant and also for the transplantable entity which, prospectively, is to be transplanted. For instance, the present invention provides means for assisting a surgical transplant team to make better and faster decisions in regard to intended transplant procedures. These procedures include the implantation of prostheses, reimplantation of expanded autogenous tissues, with or without prosthetic scaffolds, human allograft transplants and especially, xenotransplantation. In this exemplary application, the invention can radically change the manner in which matching data, concerning a transplantable entity and its source and similar data on a potential recipient, is processed and managed by a supplier and the way both sets of data, which may well exceed 100 items, are presented to and considered by, a transplant team.

According to a first and most important aspect of the presented invention, a quantitative, visual, system for integrating and presenting multiple complex variables comprises a plurality of solid, primary, three-dimensional helical structures. The helixes are preferably, but not necessarily, regularly polygonal. The helixes are adapted so that multiple species and subsets of data, intended to characterize a single complex entity, may be superimposed upon them. In an exemplary application, the field of human and animal transplantation, these data species would include multiple anatomical morphological and functions markers and multiple histocompatibility factors for a potential recipient, a transplantable entity, and where appropriate, the source of the transplantable entity.

According to a second important aspect of the present invention, adaptations of the helical structures are in the form of a series of radially arranged, primary zones, each of which is dedicated to the superimposition of a single data subset relating to a single parameter or criterion describing or characterizing the complex entity from which the data is derived. The primary zones of a most preferred, substantially regularly polygonal embodiment are defined by their radial boundary lines, the included angle therebetween and straight lines which join the intercepts of the radial lines in a first case with an outer bounding cylinder and in a second case with an inner bounding cylinder. The radial lines lie in the same plane as the surfaces which define each end of the bounding cylinders of each helical structure and it is to be understood that the surface described by the primary zones is thus a contiguous series of substantially similar, nearly trapezoidal shapes.

Cylindrical embodiments are similar, except that the intercepts of the primary zones with the outer and inner bounding cylinders are circular arcs and the primary zones, thus formed, are substantially annular sectors.

It is desirable that each primary zone is labelled near and outside its external bounding margin to readily identify the matching parameters which any data, superimposed upon it, represents. In the exemplary application, this might indicate one type of human lymphocyte antigen (HLA), a vessel diameter, or the volume of an organ.

According to a third important aspect of the invention, each primary zone is provided with a series of secondary zones, defined by lines which extend between corresponding points disposed equidistantly along each radial line defining the primary zones. It will thus be understood that in polygonal embodiments, secondary zones are a substantially trapezoidal series within each primary zone and in cylindrical embodiments, they are substantially a sector series. The secondary zones in each respective primary zone are conveniently, but not necessarily, 10 in number.

Secondary zones are used for superimposition of data to an extent which reflects the quantitative status of the matching criterion or parameter to which the primary zone is allocated. It is most important to note that the units of measurement for different matching parameters may vary. For instance, in the exemplary application, the measurement for organ volume should be in cubic measure, whereas HLAs should be indicated by a titre and vessel diameters should be in linear measure. The equidistant spacing of the limiting lines for the secondary zones, along the primary zone radial boundaries, is important. In marked contradistinction to prior art systems, the present invention uses the secondary zones and particularly the limiting lines thereof, as an arbitrary, unifying, and quantitative scale for superimposed data, regardless of the native units of the data species. The scale may be linear, logarithmic or have any other rational basis.

According to a fourth important aspect, data may be superimposed upon secondary zones within each primary zone using a grey series or advantageously, a color series. The utility of the visual arbitrary, unifying, and quantitative scale formed by the limiting lines of the secondary zones on the radial boundaries of the primary zones may be enhanced by using discrete, progressively deepening or lightening shades of grey or color, in each successive secondary zone from the inner boundary.

Each primary zone may be allocated a different color scale, however, further advantage is conferred by grouping related data subsets in a series of primary zones and using related color scales. For instance, in the exemplary application, a series of immunological parameters might be indicated by a succession of green shades passing to a succession of yellow shades. Similarly, a series of related anatomical parameters might be indicated by a succession of pink shades passing to a succession of mauve shades.

A quantitative visual system, based on the present invention, provides suppliers and their client groups, dealing in highly complex entities, especially items such as biological products and transplantable items, with an improved method for exchanging complex information quickly. The helical structure of the instant invention provides novel means for both client and supplier to view and consider, quickly and easily, a larger range of data species and a larger number of data subsets than has been possible with prior art systems. Suppliers using the instant invention are also provided with improved means for managing complex, dynamic inventories, thereby benefitting the management of their enterprise and also, ultimately, the consumers of their products.

According to a preferred method of use of the present invention, the helical structures and their primary and secondary zonal adaptations, may be reduced to a virtual format, by electronic means and may be manipulated in a suitable computer with the intention that a large number of parameters, characterizing a complex customer need, may be reduced to a representative form as a first helix, and readily compared with equally complex products reduced to a representative form as a second helix, using equivalent parameters.

It is therefore a principal object of the present invention to provide means for managing large numbers of data subsets of varied data species which characterize highly complex entities and for facilitating integrated, visual, quantitative, as well as qualitative, comparisons between such entities.

It is a further object of the present invention to provide improved means for communicating data between a supplier of highly complex products and a user whose needs require close matching of such products to their applications, thereby enabling the supplier to assist client groups in the selection process.

It is yet a further object of the present invention to provide means for controlling inventories of highly complex products, particularly biological products.

Further, the visual, quantitative, basis of the instant system provides means for enhancing the quality and speed of decisions reached by those who use the system in situations where time is the essence.

Other features, objects and advantages will become apparent from the specification and drawings in which:

BRIEF DESCRIPTION OF THE DRAWINGS

FIG. 8b is a top plan view of the upper-most revolution of a helical structure (not shown), as it is intended to be seen during the use of the alternate embodiment of the present invention in conjunction with FIG. 8a.

DETAILED DESCRIPTION OF THE PREFERRED EMBODIMENTS

With general reference of FIGS. 1–7b, there is provided a system, according to the present invention, which includes structurally based, visual means which may be employed in managing multiple data species and large numbers of data sets, used to characterize multiple complex entities and for making integrated, visual, comparisons between such entities on a quantitative, as well as qualitative, basis, and designated, in general, by the numeral 10. In an exemplary application, fully described hereinafter with particular reference to FIG. 1, the system is used for comparing complex matching data relating to a transplantable entity, to similar data on a potential patient, for use by a transplant team caring for the latter and a supplier providing the former.

Most Preferred Embodiment

Figure 2:
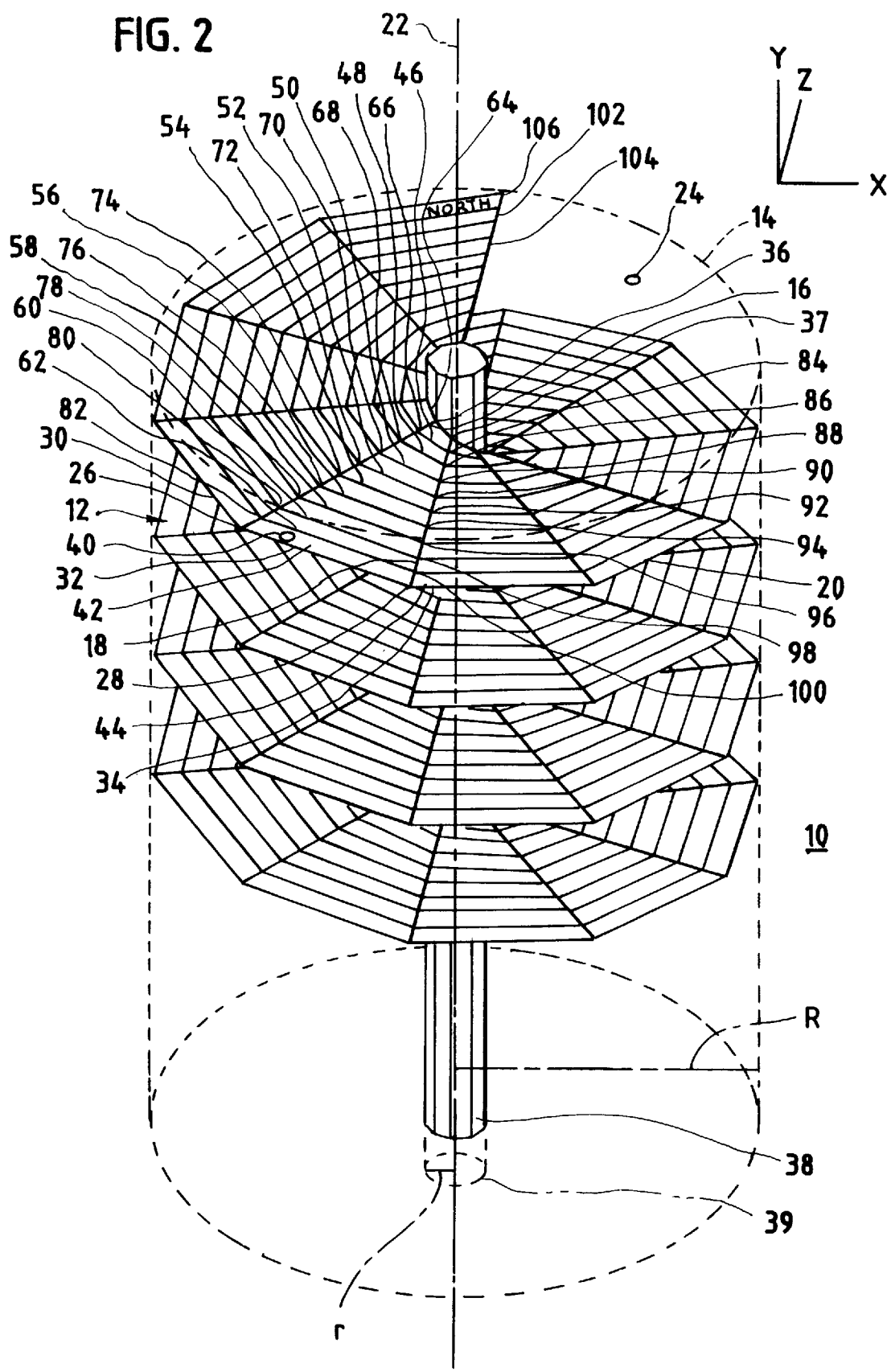
FIG. 2 is a perspective view of a most preferred embodiment of a modified helical structure, adapted so that multiple species and subsets of data, intended to characterize a single complex entity, may be superimposed upon it.

The core of the instant visual comparison system 10 is best represented is FIG. 2, which is a perspective view of a solid, three-dimensional structure 12. Structure 12 is helical and has 'N' revolutions, where 'N' is an integer which will generally be between 1 and 10. In the representation of FIG. 2, N=4. In this most preferred embodiment, helical structure 12 is substantially regularly polygonal, with 'n' included angles and 's' sides per revolution, where 'n' and 's' are integers which are equal and will generally be between 10 and 25. The notional bounding cylinder 14, partially defining regular polygonal helical structure 12, is shown by way of a dashed line in FIG. 2 and has a radius 'R', which may be of any suitable dimension. It is to be understood, as will hereinafter be fully described, that in use, structure 12 will ultimately be deployed in plurality.

Regular polygonal helical structure 12, is adapted so that multiple species and subsets of data 'S', intended to characterize a single complex entity, may be superimposed upon it. Lines, indicated by way of example at 16, 18 and 20, are radial to notional external bounding cylinder 14 and are also at right angles to its long axis 22, indicated with a center line. Lines 16, 18 and 20 also lie in the same plane as the surfaces which define each end of notional bounding cylinder 14, exemplified at 24. Radial lines 16 and 18 make intercepts with outer notional bounding cylinder 14, at 26 and 28, respectively. Intercepts 26 and 28 also lie at the apexes of angles formed by respective pairs of adjacent sides 30, 32 and 32, 34, of substantially polygonal helical structure 12. Similarly, lines 16 and 18, make intercepts 36 and 37, with notional inner bounding cylinder 39, shown by way of a dashed line in FIG. 2. Intercepts 36 and 37, also lie at the apexes of angles formed by pairs of adjacent sides of an inner, bounding, regular polygonal cylinder 38, co-axial with notional outer bounding cylinder 14.

It will be appreciated that inner bounding polygonal cylinder 38 is circumscribed by notional normal cylinder 39, which has a radius 'r'. The sides of inner bounding polygonal cylinder 38 are parallel to the sides of the helical structure 12. The surface 40 of helical structure 12 is thus described by the radial lines exemplified by 16, 18 and 20, its outer bounding, polygonal, helical structure sides exemplified by sides 30, 32, 34, and the inner bounding regular polygonal cylinder 38. Surface 40 of the helical structure 12 is thus a series of contiguous, substantially trapezoidal zones, indicated, by way of example, at 42 and 44 and hereinafter referred to as 'primary zones'. It will be understood that the number of primary zones in each revolution of the helical structure is equal to the number of included angles formed by the lines 16, 18 defining the primary zones in each revolution of the polygon; this number may be designated 'n'. It will be understood that the total number of primary zones, 'Z', is equal to the number of included angles multiplied by the number of revolutions, hence Z=nN.

Intercepts 26, 36, 28 and 37, of radial lines 16 and 18, respectively, on notional bounding cylinders 14 and 39, and radial lines 16 and 18, themselves, together with the included angle between them, define primary zone 42.

In all preferred embodiments, radius 'R' will largely determine the size of primary zones, though this will be influenced, to some extent, by radius 'r'. In general, the larger 'R' is, the larger 'n' can be without rendering any data, superimposed thereon, too difficult to see or interpret. When 'n' is large, 'N' can be smaller for any given number of data sets which are required to be superimposed and this has implications for the ultimate appearance of the structure. 'R' can be very large in an original structure but the aim should be to provide an ultimate representation of the structure in which this figure lies between 50 mm and 75 mm. The ratio of 'R' to 'r' should generally be close to 10:1. It is to be understood that in FIG. 2, notional bounding cylinders 14 and 39, are not part of helical structure 12 but are illustrated because of their defining roles.

Each primary zone is subdivided into '$n^1$' secondary zones by the provision of secondary lines which extend between corresponding points, spaced equidistantly along the radial boundary of each primary zone. As may be seen from the example in FIG. 2, conveniently but not necessarily, '$n^1$=10.

The secondary zones of primary zone 42, are defined by outer boundary line 32, secondary lines 46–62 and inner boundary line 64. Secondary lines 46–62, extend between points 66–82, on line 16 and corresponding points 84–100 on line 18. The secondary zones, within each primary zone, thus constitute a group of substantially trapezoidal areas, progressively increasing in size, with increasing distance from axis 22, of inner bounding cylinder 38.

Polygonal helical structure 12 is a solid and the pitch 'P', between revolutions 'N' may be of any convenient dimension which allows the primary and secondary zones to be seen clearly, by an observer, moving around axis 22 of notional bounding cylinders 14, 39 of helix 12 or before whom helical structure 12 is rotated about this axis 22. In practice, in an ultimate representation, the pitch 'P' should optimally be set between 35 mm and 50 mm. These recommendations should be viewed against those for 'R', but where 'R' is larger, 'P' may be larger. A satisfactory working ratio for 'R' to 'P' is 1.5:1. The general expression for the number of revolutions required is: N=S/n, where S represents the total number of species of data to be represented. 'N' must always be rounded up to the next whole number such that nN≧S.

For convenience and the establishment of good practice, it is recommended that polygonal helical structure 12 is always generated with the same rotation and that it is oriented, in a standardized manner, with respect to a conventional Cartesian coordinate system. Optimally, helical structure 12, is viewed oriented with axis 22 lying on the 'y' axis and boundary 102 up the uppermost primary zone 104 lying along the 'z' axis. Either 102, or its intersection 106, with notional outer bounding cylinder 14, may be given a convenient orientation reference such as 'North', as indicated in FIG. 2. A coordinate indicator is provided at the upper right of FIG. 2.

Polygonal helical structure 12 and its primary and secondary zonal elements, may be reduced to an electronic format in a computer and may be manipulated therein, as amplified hereinafter.

Figure 3A:
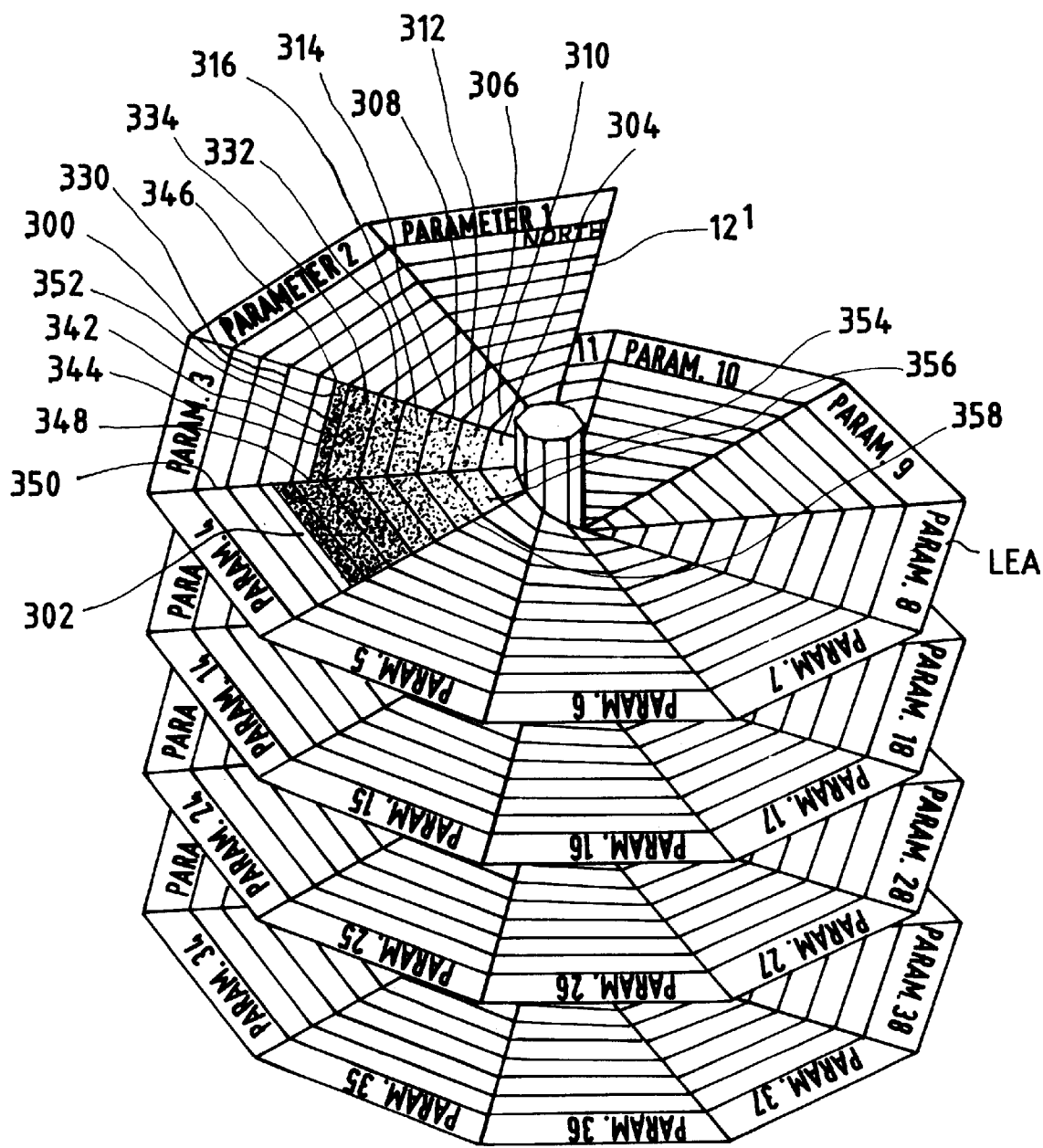
FIGS. 3a and 3b are perspective views of a most preferred embodiment in which polygonal, helical, radially-zoned structures are employed for representing multiple data subsets, each relating to matching parameters for complex entities. For clarity, parameters 1–2 and 5 and greater are left blank, and two exemplary data subsets are shown.
Figure 3B:
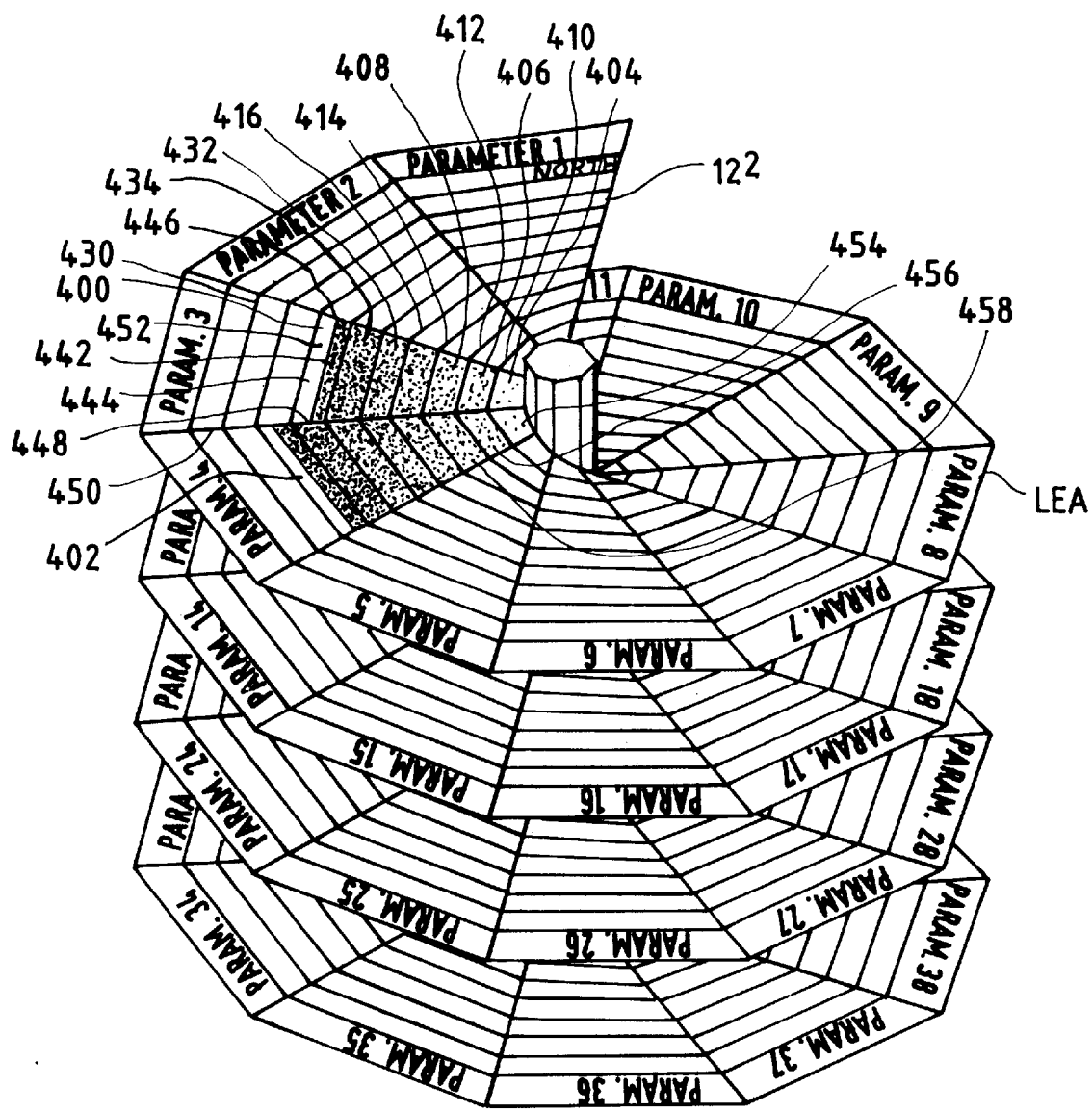

Turning now to FIGS. 3a and 3b, there are shown substantially identical paired adaptations of the polygonal helical structure 12, of FIG. 2, which are generally designated $12^1$ and $12^2$, respectively, in which each primary zone is intended to represent one matching parameter, judged as important. Advantageously, each primary zone may be provided with a labelling extension area 'LEA' and that this should lie, preferably, outside its outer bounding margin. Each labelling extension area LEA is labelled to indicate precisely which parameter it presents. Helical structures $12^1$ and $12^2$ both have primary zones with labelling extension areas generically labelled 'Parameter 1' to 'Parameter 40' (though not all labels are visible in FIGS. 3a and 3b) to represent data subsets which may be superimposed on the structure.

In practice, labelling should be specific for each parameter and not generic. This is because the complexity of the data and the number of subsets thereof, is such that it would be unwise to try to commit a coded list of parameters to memory, especially in a life-critical or mission-critical situation. Using the instant system in conjunction with generic labels and a code list would partially defeat the integrating purpose of the parameter on each label, although this should not be relied upon as the only conventional list information to be supplied.

For reasons of clarity, only two data subsets are superimposed and indicated, in each of FIGS. 3a and 3b, at 300 302 and 400, 402, respectively, and these relate to generic Parameters 3 and 4, in each helical structure $12^1$, $12^2$, respectively. It is critical that the relative position selected for any given parameter is the same in the structure used for superimposing client data as that used for superimposing data relating to the supplier's product entity. The secondary zones within each primary zone are used to indicate or represent the quantitative value of the matching parameter concerned.

It will be appreciated that the units of measurement for different parameters may vary. It is an important feature of the present invention that, in marked contradistinction to prior art systems, secondary zones, indicated by way of example at 304–308 and 404–408, in FIGS. 3a and 3b, may be used as visual means for presenting quantitative units in a progressive and unifying manner. Furthermore, because the radial extents of all secondary zones, are equal, limiting lines, exemplified at 310–316 and 410–416, together with radial boundary lines 330 and 430, furnish scale means. These scale means may be linear, logarithmic or may have any other rational basis. It will now be apparent that single radial boundary scale lines, exemplified by 330 and 430, may provide scale means which indicate one native unitary basis on a first side for one parameter and quite a different unitary basis on a second side of the same line for another parameter measured in different units.

In general, the number of secondary zones used, '$n^1$', will be 10. This is because decimal, base 10 and power 10, scales are readily and universally understood and their employment imparts greatest utility and ease of use to the instant system. The instant scale means provide visual, unifying means, whatever the underlying unitary bases of measurement may be for any and all superimposed data relating to parameters considered important in transactions between clients and suppliers dealing in highly complex products.

Data is superimposed on each primary zone in a distinctive visual manner. Each secondary zone which is superimposed with data is marked by means which give an additional indication of the quantitative value of the parameter allocated to the primary zone in which it is located. These means may be in the form, for instance, of a series of graduated grey shades, increasing in shade intensity with increasing distance of the secondary zone from the inner boundary. This method is used for secondary zones 332, 334, 432 and 434, superimposed on structures $12^1$, $12^2$, respectively. Although it may appear that the order of shade intensity may be reversed, this is counter to logic and is not recommended. Since most parameters will have superimpositions to a greater or lesser extent, most secondary zones closer to the long axis of the helical structure will be superimposed. Intense shading, in these secondary zones closer to the long axis of the helical structure, could obscure rather than emphasize differences between parameters.

Advantageously, data superimposed on each primary zone may alternatively be allocated a different dedicated color. Within any primary zone, each secondary zone, which is superimposed with data, may be shaded with color, the color progressively intensifying with increasing distance of each secondary zone from the inner boundary to indicate increasing quantitative value. As for the system utilizing grey scale shading, it is not recommended that the order of color intensification be reversed.

If the quantitative value of the data relating to a given parameter is such that, when superimposed on a secondary zone, the zone would not be fully occupied, this may be indicated, advantageously, by limiting the extent of the 'highest value' shaded areas, shown at 342 and 442. The limit line 344, of shaded data area 342, extends between points 346 and 348, on bounding radial scale lines 330 and 350 and the limit line 444, of shaded area 442, extends between points 446 and 448 on bounding radial scale lines 430 and 450, in FIGS. 3a and 3b, respectively. In FIG. 3a, points 346 and 348, indicate the quantitative scale value for Parameter 3 and shaded area 342 thus does not occupy the entire secondary zone 352. In FIG. 3b, the position is similar but in most cases not identical, with shaded area 442 and it should be noted that points 446 and 448 occur at somewhat different relative positions, on bounding radial scale lines 430 and 450, to those of points 346 and 348 on lines 330 and 350. The total value of Parameter 3, in each case, may be readily deduced from the number of secondary zones fully and partially occupied, the scale value indicated by the extent of their radial boundary lines and the positions of the points thereon, which define the limit lines of the 'highest value' shaded data areas.

Yet further advantage is conferred by grouping related parameters and superimposing their data on a series of adjacent primary zones and using related color scales to mark them. In each case, secondary zones, superimposed with data, would be quantitatively characterized by progressive saturation of the tint with increasing distance of each zone from the axis of the helical structure.

Irrespective of whether color graduations or grey graduations are employed, it is desirable that, as indicated at 354, 356 and 358, in FIG. 3a and at 454, 456 and 458, in FIG. 3b, each corresponding shaded superimposed data set is allocated a single discrete shade density for each secondary zone, rather than using a continuous graduation in shade across the zones. By this means, maximum emphasis is placed on the unifying arbitrary scale feature, with consequentially greater visual signalling of the quantitative basis of information presented for each parameter.

It will now be appreciated why most preferred embodiments of the structure 12, of the present invention, require an inner bounding polygonal cylinder 38, best seen in FIG. 2. This is to ensure that data superimposed on the innermost secondary zone of any and all primary zones may be clearly viewed. It is only minimally less advantageous that 38 is a normal cylinder. However, if no inner bounding cylinder was deployed in the structure, difficulty in viewing the innermost secondary zone would detract from the overall utility of the system.

Figure 4A:
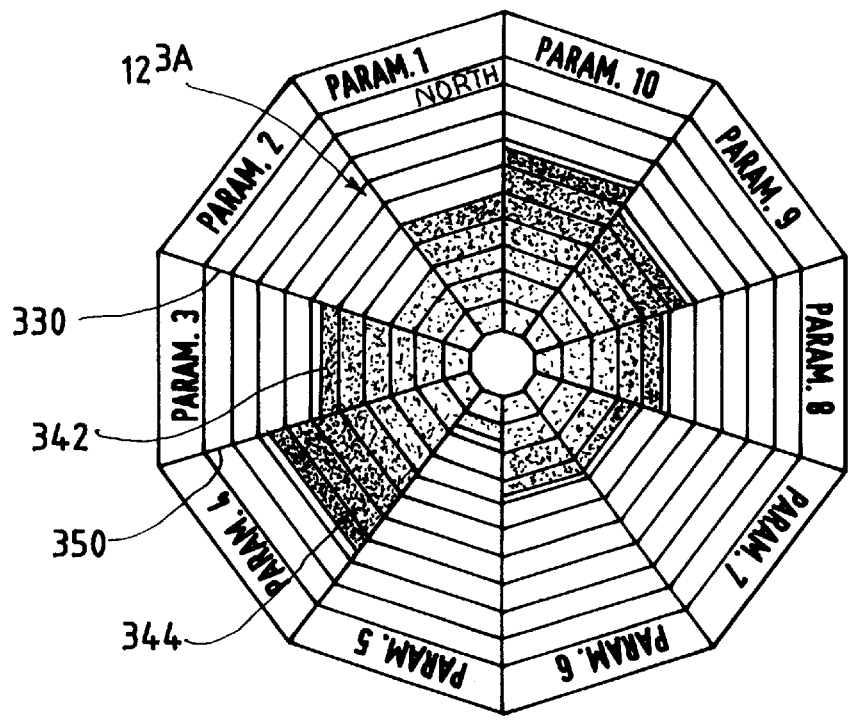
FIGS. 4a and 4c are top plan views of the upper-most revolution of the helical structures and data subsets of FIGS. 3a and 3b, respectively, as they are intended to be seen during use of the instant system. In addition to the data for parameters 3 and 4, data is shown represented by shading in primary zones corresponding to parameters 1–2 and 5–10 in order to better demonstrate the use of the system of the present invention.
Figure 4B:
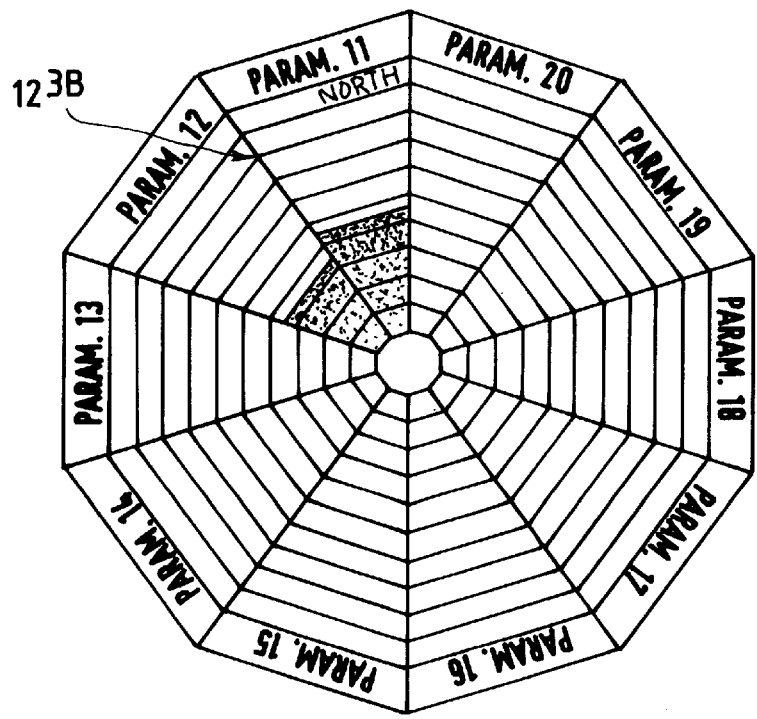
FIGS. 4b and 4d are plan views of a lower revolution of the helical structures of FIGS. 3a and 3b, as they are intended to be seen during use of the instant system. Data is shown represented by shading in primary zones corresponding to parameters 11 and 12.
Figure 4C:
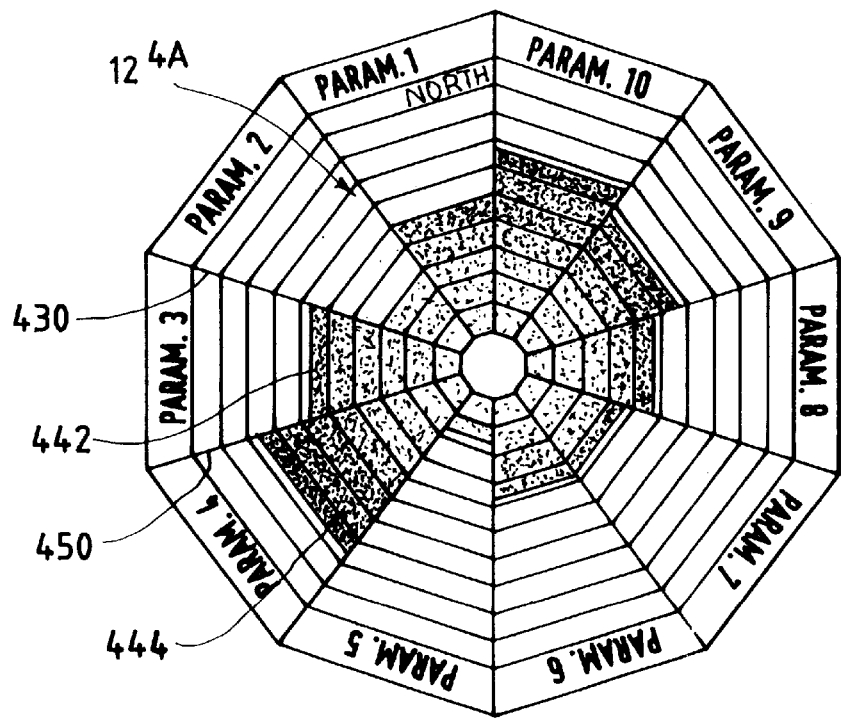
Figure 4D:
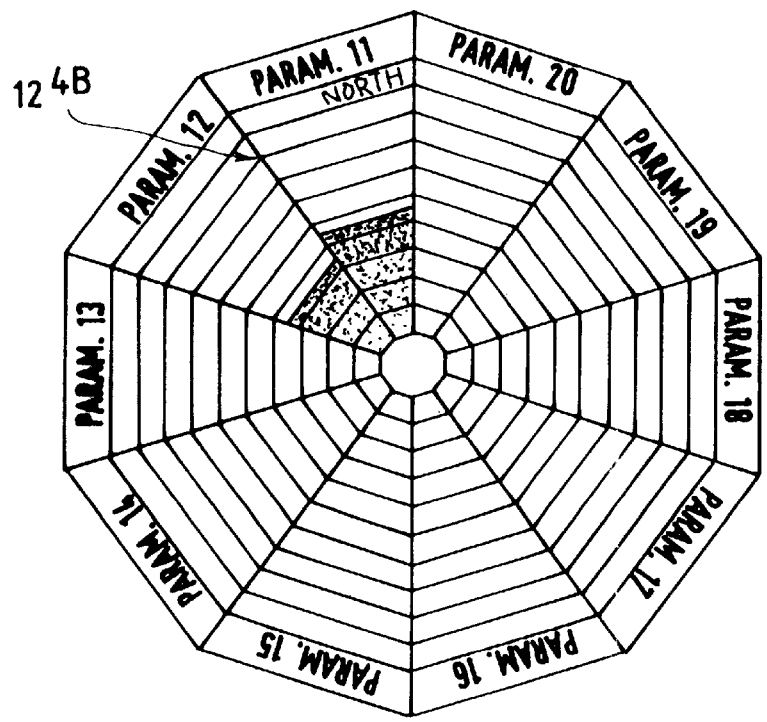

In practice, it is intended that the information held in the instant system should be presented as one or more plan views. In this context, the term 'plan view' is to be taken as meaning the view which would be obtained by looking down from the top of the long axis of the bounding cylinder of each structure. In FIGS. 4a and 4b, there is shown, in diagrammatic from, a pair of plan views of a split structure, represented by $12^{3A}$ and $12^{3B}$. The bounding cylinders are not represented in FIGS. 4a–4d and the long axis is the unlabelled center point of each plan view. These views relate to a variant of the system which requires structures where N=2, n=10 and $n^1$=10. The structures in FIGS. 4a–4b and 4c–4d have been split into individual complete revolutions. There are exactly 10 primary zones per revolution and 20 in all, providing capacity, in this example, for 20 matching parameters.

The parameters are generically labelled in each pair of plan views, both of which are in the 'North orientation', hereinbefore described. Structure $12^{3A}$, $12^{3B}$ receives superimposed data from the client and structure $12^{4A}$, $12^{4B}$ receives superimposed data from the supplier. In primary zones which have parameter entries, data are superimposed on secondary zones, according to their quantitative values, in the form of a series of discrete, shaded, grey areas. There are significant similarities between plan views $12^{3A}$ and $12^{4A}$ and between plan views $12^{3B}$ and $12^{4B}$, indicating a relatively good match.

Figure 5A:
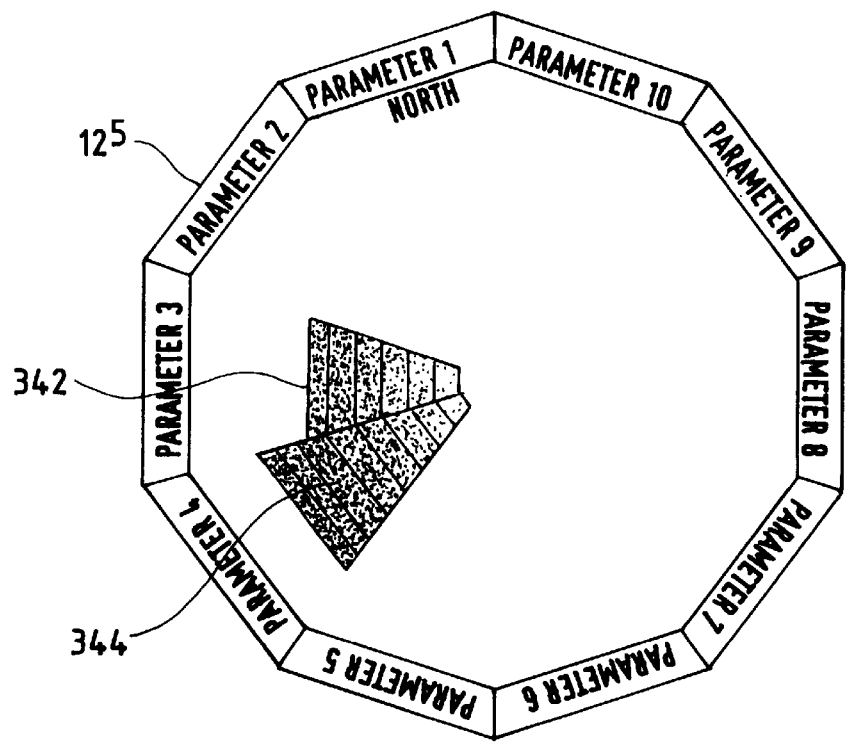
FIGS. 5a and 5b show two exemplary data subsets of the upper-most revolution of the helixes shown in FIGS. 3a and 3b, constrained by the structures thereof but without their being delineated.
Figure 5B:
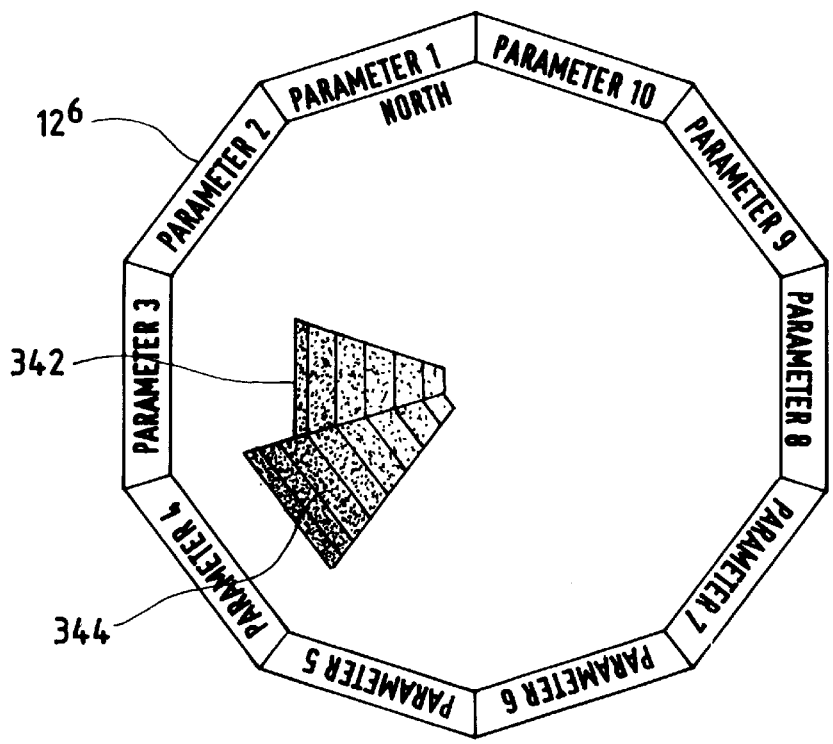

In certain circumstances it may be acceptable or even desirable that, in preferred practical embodiments, the structures should be capable of being presented both with and without visible delineation of the primary zone radial boundaries and the secondary zone boundaries which extend between them. An example of where non-delineated use might be used is when a quick overview comparison is required. It will be understood that the principal indicators of quantitative scale (the primary zone radial boundary lines and the secondary zone boundaries) will not be seen in these circumstances and these representations of the structures should be regarded only as an auxiliary utility. Reference to FIGS. 5a and 5b, shows the non-delineated condition in structures $12^5$ and $12^6$, which are otherwise substantially identical to structures $12^{3A}$ and $12^{4A}$, of FIGS. 4a and 4c, respectively, to which they should be compared (except that, for clarity, only parameters 3 and 4 are shown in FIGS. 5a and 5b). When the instant system is in use, it is the association of multivariate, complex, quantitative information and the view of it which the underlying structure provides, which are of primary importance. The physical expression of the structure or its virtual equivalent, is critical but the geometrical expression of the boundaries which define it, may be de-emphasized, with caution, on occasion.

Preferred Embodiment

Figure 1:
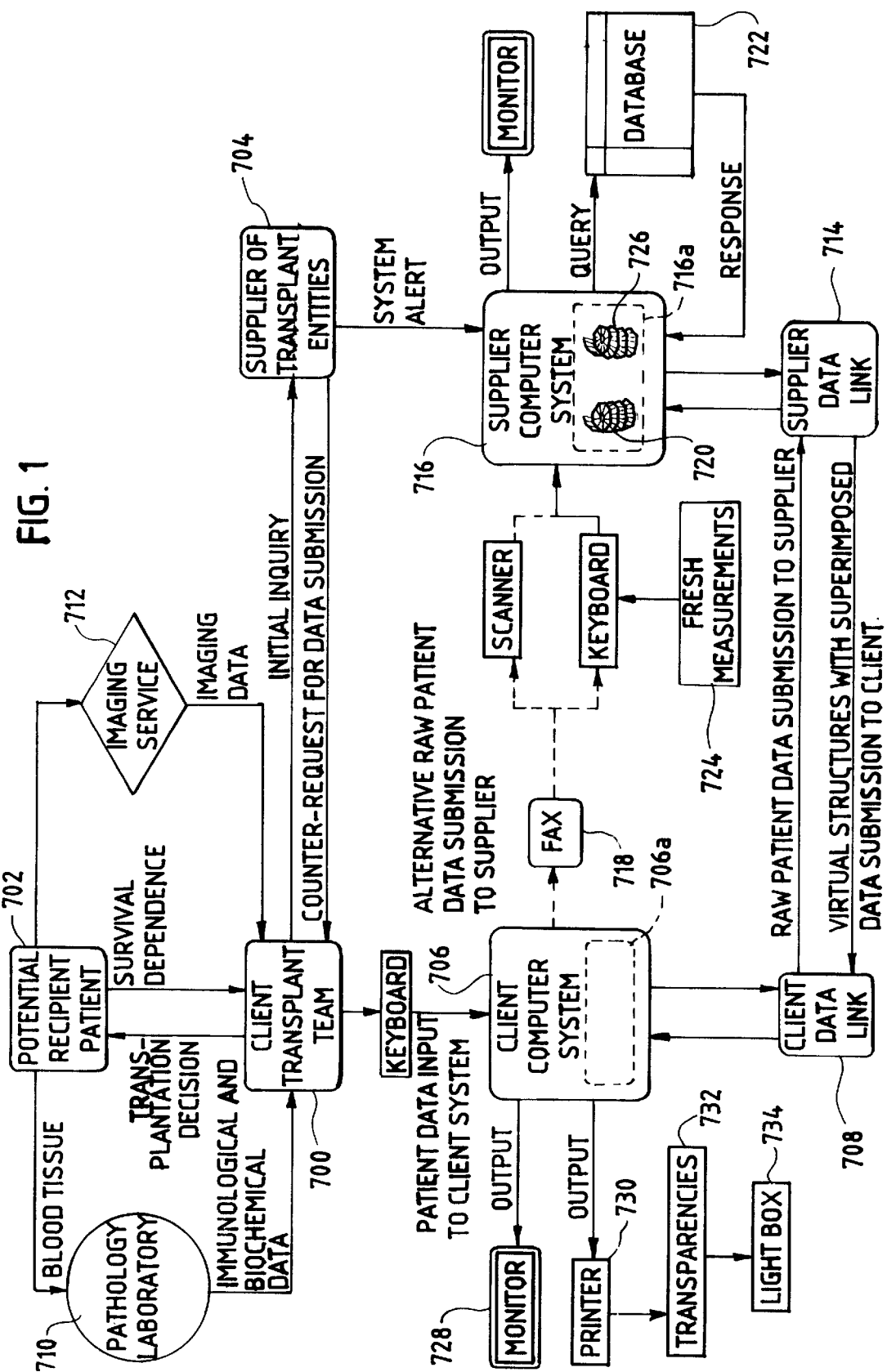
FIG. 1 is a schematic block diagram indicating the general method of use and role of the structurally based visual comparison system of the instant invention to the collection, processing and dissemination of the information used in an exemplary application of matching a prospectively transplantable entity to a potential recipient patient.
Figure 6:
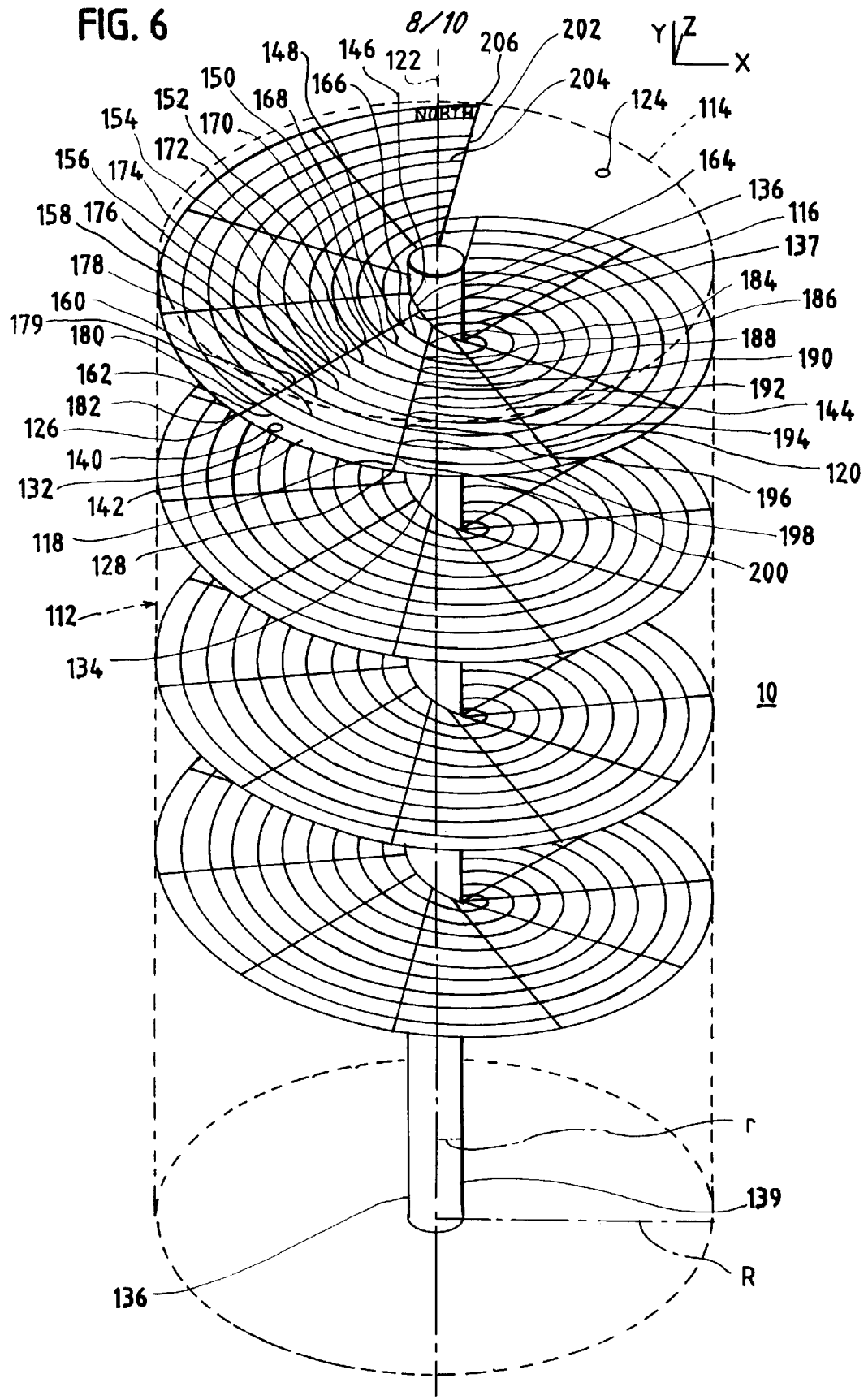
FIG. 6 is a perspective view of a preferred embodiment of a helical structure, adapted so that multiple species and subsets of data, intended to characterize a single complex entity, may be superimposed upon it.

Turning now to FIG. 6, there is shown another embodiment of the instant invention, in which system 10, of FIG. 1, has at its core, a solid, three-dimensional structure 112. Helical structure 112 is adapted, in a novel manner, so that multiple species and subsets of data 'S', intended to characterize a single highly complex entity, may be superimposed upon it.

Like structure 12 of FIG. 2 helical structure 112, has 'N' revolutions, where 'N' is an integer which will generally be between 1 and 10. In the representation of FIG. 6, N=4. In this embodiment, helical structure 112, is substantially cylindrical and is limited in its radial extent by its bounding cylinder 114, having a radius 'R', which may be of any suitable dimension. It is to be understood that, as with structure 12, of FIG. 2, 112, will ultimately be deployed in plurality.

Helical structure 112 is not modified by the provision of polygonal sides. In FIG. 6, boundary lines, indicated by way of example at 116, 118, and 120, are radial to external bounding cylinder 114 and are also at right angles to the long axis 122, of 112. Additionally 116, 118 and 120, lie in the same plane as the surfaces which define each end of bounding cylinder 114, exemplified at 124. In this embodiment, lines 116, 118, intercept external bounding cylinder 114, at 126 and 128, respectively. There are 'n' equal included angles between radial lines, exemplified by 116 and 118, per revolution, where 'n' is an integer which will generally be between 10 and 25. In the representation of FIG. 6, n=10. It will be understood that the total number of primary zones 'Z' is equal to the number of included angles multiplied by the number of revolutions, hence Z=nN.

Lines 116, 118 intercept a second, inner bounding cylinder 139, at 136 and 137, respectively. Inner bounding cylinder 139 is co-axial with outer bounding cylinder 114 and has a radius 'r'. In such embodiments, the inner and outer bounding cylinder are substantially circular arcs which lie within the surfaces of the inner and outer bounding cylinders, respectively and the primary zones, thus formed, are substantially annular sectors. The surface 140, described by the radial lines exemplified by 116, 118 and 120, the outer bounding circular arcs 130, 132, 134 and inner bounding cylinder surface 136 is thus a series of contiguous primary zones, each of which is substantially an annular sector, indicated, by way of example, at 142 and 144.

Intercepts 126, 136 and 128, 137 of radial lines 116 and 118 on bounding cylinders 114 and 139, respectively, radial lines 116 and 118, themselves, together with the included angle between them, define primary zone 142.

As hereinbefore described, in all preferred embodiments, radius 'R' will largely determine the size of primary zones, though this will be influenced, to some extent, by radius 'r'. In general, the larger 'R' is, the larger 'n' can be without rendering any data, superimposed thereon, too difficult to see or interpret. When 'n' is large, 'N' can be smaller and this has implications for the ultimate appearance of the structure. 'R' can be very large in an original structure but the aim should be to end up with an ultimate representation in which this figure lies between 50 mm and 75 mm. The ratio of 'R' to 'r' should generally be close to 10:1.

Each primary zone is subdivided into '$n^1$' secondary zones by the provision of secondary lines which extend between corresponding points, spaced equidistantly along the radial boundary of each primary zone. Conveniently but not necessarily, '$n^1$'=10. As hereinbefore stated, with reference to the most preferred embodiment, the number of secondary zones used, '$n^1$', will generally be 10. This is because decimal, base 10 and power 10, scales are readily and universally understood and their employment imparts greatest utility and ease of use to the instant system.

As may be seen from continuing reference to FIG. 6, 10 secondary zones are depicted for each primary zone. The secondary zones of primary zone 142, are defined by outer circular arc boundary 132, secondary circular arc lines 146–162 and inner circular arc boundary 164. Secondary circular arc lines 146–162, extend between points 166–182, on line 116 and corresponding points 184–200, on line 118. Secondary circular arc lines 146–162, are parallel to and follow the planar paths of outer and inner circular arc boundaries 132, 164. The secondary zones, within each primary zone, thus constitute a group of substantially annular sectors, progressively increasing in size, with increasing distance from axis 122, of inner bounding cylinder 139.

Helical structure 112, is a solid and the pitch 'P', between revolutions 'N' may be of any convenient dimension which allows the primary and secondary zones to be seen clearly, by an observer, moving around axis 122, of bounding cylinders 114, 139, of 112 or before whom 112, is rotated about this axis. In practice, the pitch P should be set between 35 mm and 50 mm, in an ultimate representation. These recommendations should be viewed against those for 'R'; where 'R' is larger, 'P' may be larger and the converse applies. In a non-limiting manner, a satisfactory working ratio for 'R' to 'P' is 1.5:1. The general expression for the number of revolutions required is: N=S/n. 'N' must always be rounded up to the next whole number such that nN≧S.

For convenience and the establishment of good practice, it is recommended that helical structure 112, is always generated with the same rotation and that it is oriented, in a standardized manner, with respect to a conventional Cartesian coordinate system. Optimally, 112, is oriented with axis 122, lying on the 'y' axis and boundary 202, of uppermost primary zone 204, lying along the 'z' axis. Either 202, or its intersection 206, with outer bounding cylinder 114, may be given a convenient orientation reference such as 'North', as indicated in FIG. 6.

Reasons for Selection of Most Preferred Embodiment over Preferred Embodiment

The reason why structure 12 is preferred over structure 112 in the instant invention, relates to the unifying arbitrary scale feature provided by the radial boundary lines (which delineate primary zones) and the intercepts on them made by the secondary zone boundary lines and the inner and outer primary zone boundary lines. This may be explained with reference to FIGS. 7a and 7b, which show examples of the local conditions which obtain in these areas for the polygonal and cylindrical embodiments, respectively.

Figure 7A:
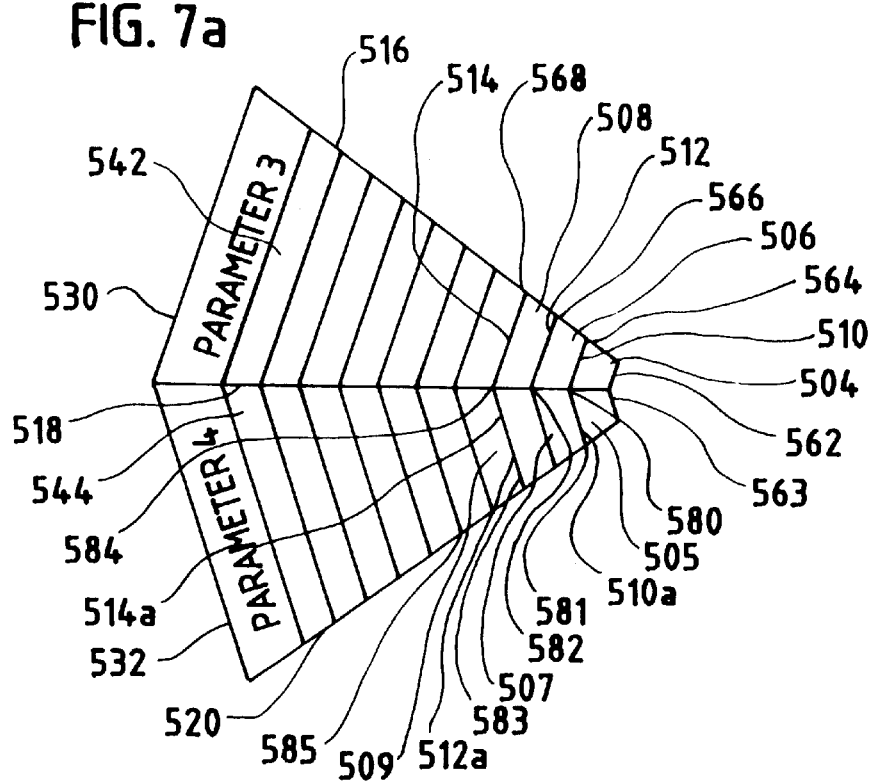
FIGS. 7a and 7b are enlarged top segmented views showing local examples of the conditions which obtain at the intercepts between secondary zone boundary lines and primary zone radial boundaries for the structure of FIG. 2 and FIG. 6 respectively.

In FIG. 7a, there is shown a partial, plan view of a regularly, polygonal, helical structure of a most preferred embodiment of the present invention, in which primary zones 542 and 544, may be seen. Primary zone 542, is defined by radial boundaries 516, 518 and outer and inner straight boundary lines 530 and 562, respectively, together with the included angle between 516 and 518. Primary zone 544 is defined similarly by lines 518, 520, 532 and 563, together with the included angle between 518 and 520.

Secondary zones, in primary zone 542, are indicated by way of example, at 504, 506 and 508 and are defined by radial boundaries 516, 518 and most particularly, in this case, by straight limiting lines 510, 512 and 514. Limiting lines 510, 512 and 514 extend between points 564, 566 and 568, disposed equidistantly on line 516 and corresponding points 580, 582, 584, on line 518. Secondary zones, in primary zone 544, are indicated by way of example, at 505, 507 and 509 and are defined by radial boundaries 518, 520 and most particularly, in this case, by straight limiting lines 510a, 512a and 514a. Limiting lines 510a, 512a and 514a, extend between points 580, 582 and 584, disposed equidistantly on line 518, and corresponding points 581, 583 and 585, on line 520. It will be noted that the secondary zone limiting lines of primary zone 542, and those of primary zone 544, meet radial boundary line 518, at similar, acute, converging angles. This is strikingly visually apparent and is a direct result of the polygonal arrangement of the basic helical structure, here seen in partial plan view.

Figure 7B:
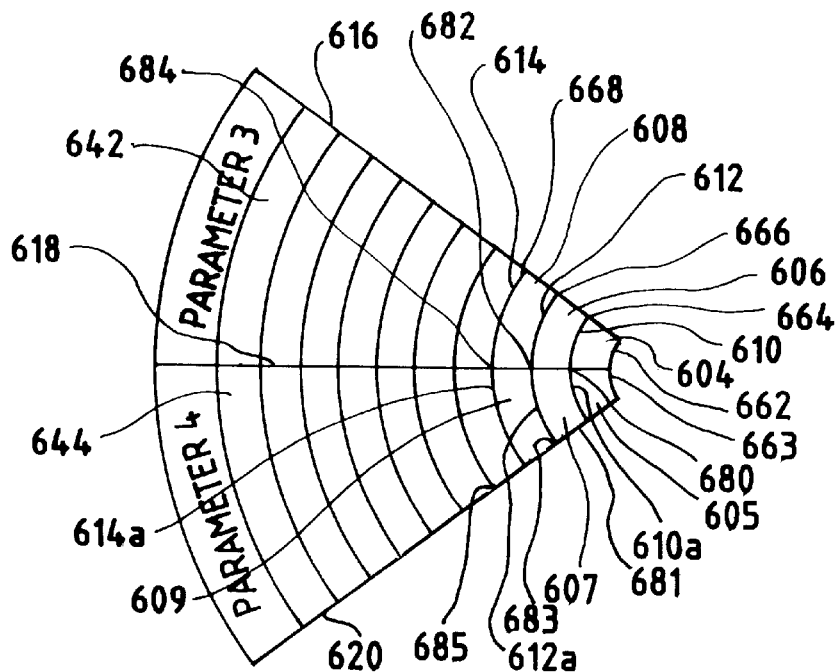

Turning, now to FIG. 7b, there is shown a partial plan view of a cylindrical, helical structure of a preferred embodiment of the present invention, in which primary zones 642 and 644, may be seen. Primary zone 642, is defined by radial boundaries 616, 618, and outer and inner straight boundary lines 630 and 662, together with the included angle between 616 and 618. Primary zone 644, is defined similarly by lines 618, 620, 632 and 663, together with the included angle between 618 and 620.

Secondary zones, in primary zone 642 are indicated by way of example, at 604, 606 and 608 and are defined by radial boundaries 616, 618 and most particularly, in this case, by circular arc limiting lines 610, 612 and 614. Circular arc limiting lines 610, 612 and 614, extend between points 664, 666 and 668, disposed equidistantly on line 616 and corresponding points 680, 682 and 684, on line 618. Secondary zones, in primary zone 644 are indicated by way of example, at 605, 607 and 609 and are defined by radial boundaries 618, 620 and most particularly, in this case, by circular arc limiting lines 610a, 612a and 614a. Circular arc limiting lines 610a, 612a and 614a, extend between points 680, 682 and 684, disposed equidistantly on line 618 and corresponding points 681, 683, and 685, on line 620.

It will be noted that the secondary zone limiting lines of primary zones 642 and 644, meet radial boundary line 618 at 90° and further, that each series of secondary zone limiting lines is effectively a circle divided into circular arcs by radial lines exemplified by 618. This is in contradistinction to and is rather less visually apparent than, the embodiment of FIG. 7a.

The effect of this difference between the two embodiments is even more marked when data is superimposed and especially so if the present invention is used without delineation of the structure. In all embodiments, the intersections of secondary zone limiting lines on primary zone radial boundary lines and radial lines, themselves, provide the feature of unifying, arbitrary, scale means. It will be apparent that highlighting means for this is important and thus it will now be understood why the polygonal helical arrangement is preferred to the cylindrical helical arrangement in the basic structure. It will also be apparent why, in all cases, delineated rather than non-delineated representations, are preferred.

Apart from the points of difference immediately hereinbefore described, the most preferred and preferred embodiments are substantially similar.

EXEMPLARY APPLICATION AND PREFERRED METHOD OF USE

Application of the Present Invention in Surgical Transplantation

The present invention may be beneficially applied in the field of transplantation surgery where it is required to compare numerous biochemical, immunological and physical factors between a potential recipient and a transplantable entity, in order to ensure that there is an acceptable match between them. In this context 'acceptable' means a match which is, in the judgment of those responsible for acquiring the transplantable entity and carrying out the procedure, likely to enhance the quality of life afterwards and/or to prolong it beyond the expected duration, were the procedure not to be carried out. The present invention is especially useful in newer and more demanding types of transplantation, such as xenotransplantation, since developments in this technology allow and indeed require, many more parameters to be considered. It is precisely this utility which the present invention offers. It is important to note that the instant invention may be applied in the field of transplants into animals, from whatever source, as well as transplants into humans. Though the field of transplantation into animals is largely experimental, it is of great importance in developing transplant technology for humans.

It will be understood, from well known principles, that any organization intending to function as a serial supplier of transplantable entities, would need to maintain a precise system of inventory control, which could be interrogated easily. Further, it will be understood, that a client transplant team or a designated representative thereof or some other person or organization, acting on behalf of such a team, would need to make inquiries to organizations which might be capable of supplying a transplantable entity required for a potential patient. Such organizations may or may not be commercial companies. Research into the prior art suggests that, up to now, a general inquiry is followed by the exchange of matching data, which is generally limited to general data and some immunological data, particularly tissue typing data. Such tissue typing data typically includes information on the human lymphocyte antigen (HLA) types and, where available, some sub-type data. This data has been exchanged using line-by-line lists, by facsimile transmission or by other electronic means. As indicated generally in FIG. 1, amplified hereinafter, the present invention 10, provides means which significantly advance the process of information exchange and further provides means for improved inventory management for the supplier of transplantable entities as well as, most importantly, providing the client transplant team with improved visual, integrated, structurally based means for quantitative and qualitative assessment of the match and likely outcome of the intended procedure.

Accordingly, a quantitative visual system 10, based on the present invention, provides suppliers and their client groups, dealing in highly complex entities, especially items such as biological products and transplantable items, with an improved method for exchanging complex information quickly. The adapted helical structure of the instant invention provides novel means for both client and supplier to view and consider, quickly and easily, a larger range of data species and a larger number of data subsets than would have been practicable with prior art systems.

Preferred Method of Use

According to a preferred method of use of the present invention, both suppliers users and client users must first be trained in the concept, principles and use of the novel adapted helical structures, using printed manuals and lectures. In routine practice, the helical structures and their primary and secondary zonal adaptations, are converted to a virtual format, by electronic means and are manipulated within computers. Data, concerning a large number of parameters, characterizing a potential transplant recipient, are collected by appropriate members of a client transplant team and provided to a prospective supplier. The supplier matches these data with data on substantially similar parameters, relating to one or more potentially suitable transplantable entities. The supplier then superimposes each data set, separately, on a virtual helical structure, according to the present invention and transmits both back to the client, so that they may be compared.

With reference first to FIG. 1, the system provides means for collating and transferring data collected by a client transplant team 700, concerning a potential recipient patient 702, to an intended supplier 704, of transplantable entities. Following an initial inquiry, from the client transplant team 700, to the supplier 704, normally by telephone, the data on the potential recipient patient 702, will be submitted by means which are typically in the form of a conventional computer 706, with appropriate software 706a and a client datalink 708. The line item data may extend to between 100 and 200 sets and possibly more. It will relate, amongst other things, to the biochemistry, immunological status and anatomy of the potential recipient patient 702. The client transplant team 700, will collect these data using a variety of laboratory services, such as a suitable pathology laboratory 710 and a suitable imaging service 712. Data is received by the supplier's datalink 714, directly into another computer system 716, with appropriate software 716a, at the supplier's premises. If the supplier 704, is amenable and the practice is for some reason, preferred or at least mutually acceptable, the data may alternatively be submitted by facsimile transmission 718, for manual or electronically scanned entry to the computer system 716, at the supplier's premises.

Once received into the supplier's computer system 716, data are superimposed on the stored virtual format of the regular polygonal helical structure, according to the present invention, indicated at 720, using suitable software means. In addition, data on the most equivalent or suitable product or products, are either retrieved by the supplier 704, from its database 722 or when applicable, input to the system from a freshly collected series of measurements 724. These data are also superimposed on a stored virtual format of the regular polygonal helical structure indicated at 726, using the same means as that for 720. Considering, briefly, FIGS. 3a and 3b, in this context, structure $12^1$, might represent a potential recipient patient and $12^2$, might represent a prospective transplantable entity.

As hereinbefore described with reference to FIGS. 3a, 3b, 4a 4d and 5a, 5b, in general use, one series of primary zones (not indicated in FIG. 1) within each of 720 and 726, is dedicated to various types of human lymphocyte antigens (HLAs) and their sub-types. Another series, in each case, represents biochemical data and yet another series, in each case, represents anatomical data. In this latter example, these data include the diameters of important vessels and required stub lengths, volume of the transplantable entity and in the case of the potential recipient, body cavity volume, coordinate data and pole-to-pole measurements. This last group of parameters is important and will become increasingly so as xenograft transplantation becomes popular because client transplant teams will be able to specify optimal requirements. By way of explanation, as genetically enhanced pigs and possibly other species are developed as potential donors of hearts and other organs, suppliers will be able to grow animals, the organs of which may be physically characterized, in detail, by imaging and by biochemical means, for 'slaughter on demand' when a potential recipient with a good match presents. Alternatively, such animals may be sacrificed to a program and the appropriate organs stored to provide a broad-based inventory, physically characterized by direct measurement and biochemically and immunologically typed. These multiple complex data are stored within the database 722 of supplier 704.

As hereinbefore described with respect to FIGS. 3a, 3b, 4a 4d and 5a, 5b, within supplier's computer system 716, each primary zone of 720, 726, is specifically labelled, in its label extension area, with the definition and measurement system applicable to the parameter, to which the data superimposed on it, refers.

Generic labelling is not recommended for any specific application though it may be employed on physical helical structures used for training potential users in the concept and principles of the present invention. The reason for this stricture is because the complexity of the data and the number of data subsets in any application will usually be large and it would be unwise for any user to try to commit a coded list of parameters to memory, especially in a life-critical or mission-critical situation. The true, conventional quantitative unitary value of each parameter is also given in each label extension area although these data are not to be relied upon as the sole source of conventional line-by-line 'list information'.

The superimposed data subsets for all data species are submitted in colors except when there are computer system limitations which prevent this, in which case grey scales are used as hereinbefore described with reference to FIGS. 3a, 3b and 4a–4d. Although the particular range of colors selected is not critical to the method of use, related data subsets, within a data species, are optimally indicated with related colors. For instance the series concerning 'immunological status' parameters could be allocated a range from, say, shades of green to shades of yellow. Similarly, superimposed data subsets for the species 'anatomical marker' parameters could be indicated with colors which could range from, for example, shades of pink to shades of mauve.

When the supplier 704, has completed matching the client requirements to its inventory, both sets of structural representations 720; 726, of the data are then submitted, by electronic means, to the client transplant team 700, using the datalinks 708; 714. As inferred above, it is important that standard and conventional, line-by-line, comparative matching data would be presented as well. There are two important reasons for this. First it provides the client transplant team 700, with means of checking that the data which was submitted to the supplier 704, has not been corrupted in transmission nor changed in any other way. The second is that certain members of the client transplant team 700 may either prefer such a presentation or may only need to consider a few of the data subsets n order to fulfil their own specific duties, in which case they may have less need for a full visual overview.

At this point it is important to note that, although for reasons of clarity, the disclosure has generally been exemplified with respect to two sets of data requiring to be represented, one from a client and one from a supplier, this may not always be the case. It is highly likely that circumstances will arise when a supplier may be able to offer two or more alternatives to a client. In such a case, a supplier would submit the appropriate number of virtual structural representations and the disclosure is to be read and understood in this light.

The matching sets of structural representations 720, 726, of the data submitted by the supplier 704, to the client transplant team 700, via datalinks 708, 714, are optimally in the form of superimpositions on the regular polygonal helical structures of the present invention. Structural representations 720, 726, are intended to be manipulated within the computer 706, of client transplant team 700, so that they may be viewed as one or more pairs of plan views, as previously described with reference to FIGS. 4a–4d. In this context, the term 'plan view' is to be taken as meaning the view which would be obtained by looking down the long axis of a bounding cylinder to the instant helical structure. The number of paired plan views required will depend upon the number of parameters which are involved and this number will be a major factor driving the number of revolutions of the helical structure in any given case. The basis of calculation for using the helical structure is hereinafter described.

Concerning some of the data species and their measurement systems in this exemplary application, a measurement for 'organ volume' will be in cubic measure, vessel diameters, vessel stub length and pole-to-pole distances will be in linear measure and that of HLAs will most likely be indicated by a titre. The unifying arbitrary scale means provided within plan views of the regular polygonal helical structures of the instant invention provide an integrated visual output for the client transplant team 700, to evaluate in 'one pass'. Returning to FIGS. 4a and 4c and discussing these in terms of this exemplary application, there is a direct visual indication that matching Parameters 3 and 4 are present in both the potential recipient structure $12^1$ and the prospective transplantable entity $12^2$ but not to an identical extent. There are ten secondary zones indicated in each of the primary zones of FIGS. 3a and 3b and if the scale is linear, the 'patient' may be seen to have scored about 67 and 77 and the transplantable entity has scored about 65 and 75, for Parameters 3 and 4, respectively. For many transplantation criteria this would be judged an excellent, though not perfect, match.

Returning to FIG. 1, in system 10, plan views of 720; 726, with the structure delineated, are output, by default, to a monitor screen 728, serving the computer system 706, of the client transplant team 700. If required, a toggle function may be provided to remove delineation. This is because, occasionally, a quick comparative overview may be desired and some individuals may wish to work without the delineated structure for this purpose. However, when this is done, the valuable integrating scale feature is partially sacrificed.

Thereafter, 720; 726, may, if so desired, be output via a printer 730, to a large format transparency 732. Such transparencies may be viewed, conveniently, on a light box 734 such as one typically used for viewing x-ray slides. However, this method is not intended to be limiting and outputs of paired views and comparisons between them, may be made in a variety of other ways. These could include stereoscopic overlays for review in a suitable device. Alternatively, other optical or electronic comparator means, may be used.

Concerning the specification of the helical structures, for a client-submitted number of data sets 'S' and a supplier-selected number of primary zones, per revolution, for data superimposition, 'n', the number of revolutions, 'N', in the structures will be N=S/n. 'N' must always be rounded up to the next whole number such that $nN \geq S$. That is in order to ensure that the structure always has sufficient capacity to accommodate the number of data sets which are to be superimposed. Although the physical helical structures are not limited in size, in practice representational size may be limited by monitor screens commonly used for viewing, by printer platen dimensions or by available transparency formats. For this reason, radius 'R', of the representations needs to be kept to a rational maximum, measured on-screen, of about 75 mm when pairs of structures are to be compared. As will have been noted in relation to both embodiments, hereinbefore described, the ratio of 'R' to 'r', is optimally about 10:1. The point of this ratio is simply to ensure that 'r', does not obtrude excessively into the data superimposition area but nevertheless is large enough the make the innermost secondary zones large enough and sufficiently delineated to be clearly visible and readable. Practical experimentation has shown that even with 'R', set at 75 mm, 'n', has a practical maximum of 25, except where very large screens or print formats are available. It will, therefore, be understood that if 'S', approaches 200, up to eight viewing plan pairs will be needed. This is practicable, particularly when the practice of grouping related data subsets within data species is adopted. However, software manipulation may be used to allow the entire helical structure pair to be displayed. By setting the pitch, 'P', at a ratio of about 0.67:1, with respect to 'R', this, too, is practicable in representations on monitor screens which are in common use. By way of explanation and using the previous example of 200 data subsets, where N=8, there will be seven pitches.

Since, in this example, where R=75 mm, P=7×75×0.67= 351.75 mm and also 2R×2=300 mm (paired structures), the entire requirement may accommodated on a 17" monitor and on x-ray format transparencies, with a modest margin. Software manipulation of the on-screen paired images may be employed to allow detailed comparisons of data species, sub species and individual parameters, to be made easily.

When the supplier 704, judges that more than one solution is possible for meeting the needs of a client transplantation team 700, a commensurately increased number of helical structures, each superimposed with appropriate data, must necessarily be employed. Under these circumstances, it will usually be the case that the representation of the data superimposed, virtual helical structure, for each proposed solution, is compared, in a serial manner, with the data superimposed, virtual helical structure, relating to the potential transplant recipient, 702.

By comparing complex information, rendered into a visual pattern, constrained by and superimposed upon the novel adapted helical structures of the instant invention and using the system of which it forms a part, the client transplant team 700, may evaluate all of the selected parameters, very quickly. By these means, the team is assisted in reaching an informed and augmented clinical decision with greater precision and subtlety than has previously been possible.

The system 10, of the present invention, is employed at the discretion of transplant team users in different ways, according to preference. Some may prefer to use its visual integrated means as a basis for quick preliminary assessments, with less quantitative information. Others may wish to obtain a comprehensive overview. Yet others may wish to make detailed comparisons of small groups of parameters or even of individual parameters. Whichever approach is selected, the instant invention provides means for enhancing, refining and facilitating the clinical and scientific judgments which must be made prior to undertaking transplantation. In addition, the invention provides suppliers of transplantable entities with novel means for controlling and characterizing inventories of these items. Both suppliers and their client transplant teams, are provided with improved and expanded means of mutual communication, thereby enhancing the likelihood of favorable outcomes for recipients of transplantable entities.

The novel means of presenting matching data employed in the instant system takes advantage of the fact that humans are highly adept in the processing and assessment of large amounts of information presented in the form of visual patterns. In the instant invention, the plural visual analogue system, based on a plurality of helical structures, can encompass multiple data species and very large numbers of data subsets, which may be viewed all at once and may be used as means for reaching decisions. The instant system provides for but does not impose, a 'one-pass', improved method of decision making in the field, for example, of surgical transplantation.

ALTERNATE EMBODIMENT AND ALTERNATE APPLICATION

The present invention as hereinbefore described, as well as certain further alternate embodiments thereof, are also particularly well suited to less-critical, although still complex, systems requiring matching of candidates to particular applications, each having multiple complex parameters. For example, in manufacturing environments, certain components are typically supplied in large quantities, with each of the components in the large supply varying slightly from one another due to normal fabrication inconsistencies. An application for the components may have numerous dimensional requirements and each such dimensional requirement typically has a range of acceptable variation, well known in the art as tolerances. It is sometimes difficult for an assembly worker to determine whether a particular component in a large supply meets each specified tolerance for all the various dimensions of the application. Installation of a component that fails to meet all tolerances may result in unacceptable defects. On the other hand, in instances where a particular component is found not to meet tolerances of a particular application, the worker may dispose of the component, which would be wasteful if that component could have been used in another particular application.

It is recognized that the present invention can be easily adapted to such a manufacturing operation in order to assist workers to more accurately determine whether a particular component falls within the specified tolerances for a given application, or to match acceptable components with applications so as to reduce waste. When each component is fabricated, the supplier can provide the component with a part number or bar code and enter the exact dimensions of each component into a computer, storing the information in a data file which is supplied to the customer manufacturer. The data may be used to construct a suitable helical structure $12^1$ according to the teachings of the present invention, graphically representing each dimension of the component in the various primary and secondary zones of the helical structure. The worker would then call up the helical structure $12^1$ corresponding to a given component by reading the part number off the component and manually entering the number into a computer, or by using a bar code reader interfaced with the computer. The worker could then compare that helical structure $12^1$ to a second helical structure $12^2$ corresponding to the given application and determine the suitability of the match.

Figure 8A:
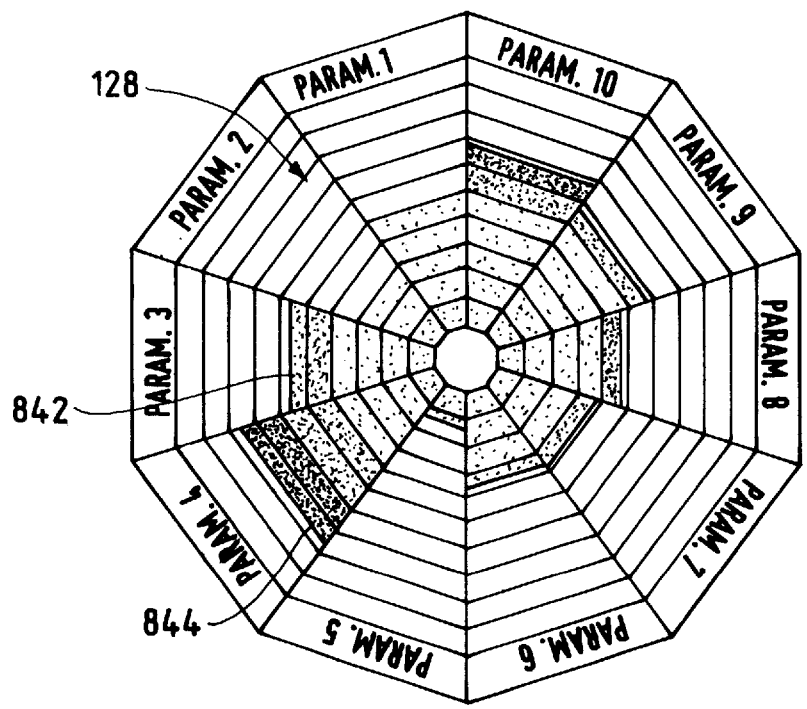
FIG. 8a is a top plan view of the upper-most revolution of the helical structure of FIGS. 3a, as it is intended to be seen during the use of an alternate embodiment of the system of the present invention. Data is shown represented by shading in primary zones corresponding to parameters 1–10.
Figure 8B:
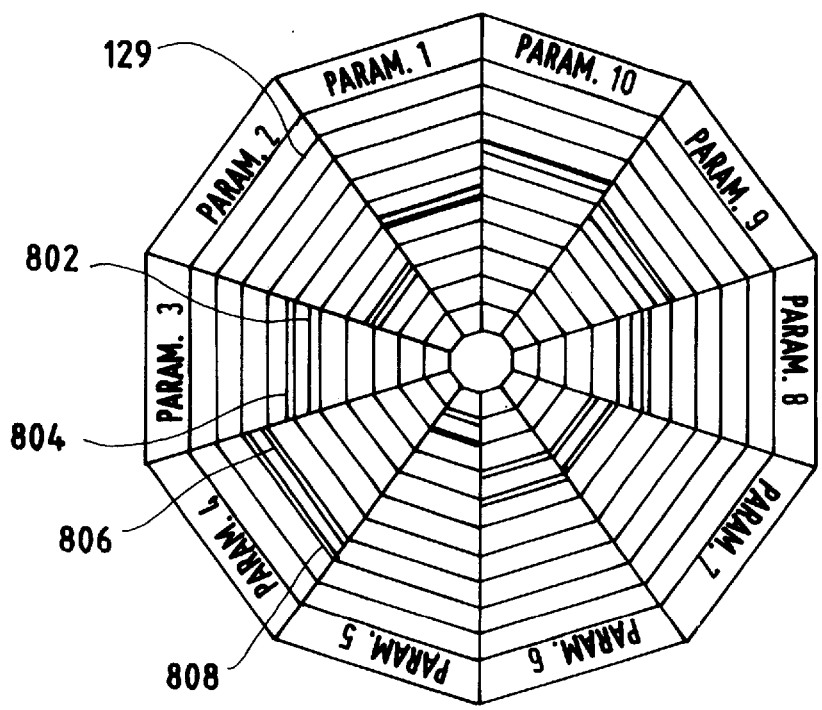

In a slightly different embodiment of the present invention, as shown in FIGS. 8a and 8b, in the helical structure $12^9$ (shown in FIG. 8b) corresponding to a given application having specified tolerances, the shading of the secondary zones may be enhanced, or even substituted altogether, by lines representing minimum 802,806 and maximum 804,808 acceptable values for the tolerances of each dimension. When the worker superimposes or overlays the helical structure $12^8$ graphically representing a certain component, he or she will readily see, by looking at whether all shaded or colored regions terminate within the tolerance boundary lines in all the primary zones, whether that component falls within the specified tolerances for the given application. So long as the quantitative value of each parameter, i.e. each dimension of the component, as designated by a limit line if that value falls somewhere other than at the end of a secondary zone, or by the end of a secondary zone, falls within the tolerance zone for that parameter (or dimension) defined by the tolerance boundary lines, the component is suitable for use in the application. I.e., if upon superimposing the revolution of helical structure $12^9$ shown in FIG. 8b onto the revolution of $12^8$ shown in FIG. 8a, the worker sees that if 842, which represents the highest value of the component's dimension represented by Parameter 3 in helical structure $12^8$, falls between 802 and 804, and 844, which represents the highest value of the component's dimension represented by Parameter 4 in helical structure $12^8$, falls between 806 and 808, then the component meets the tolerances of the application for both parameters 3 and 4.

It will be apparent to those skilled in the art that numerous modifications or changes may be made without departing from the spirit or the scope of either the present invention or its method of use. Thus the invention is only limited by the following claims.

We claim:

1. A system for comparing a plurality of complex entities wherein a first set of data concerning a set of multiple diverse parameters is used to characterize a first complex entity and one or more additional sets of data concerning said set of parameters is used to characterize one or more additional complex entities, said system comprising:

a separate helical structure for representing each of said complex entities, said helical structure being defined by an outer bounding cylinder, an inner bounding cylinder coaxial with said outer bounding cylinder and a pitch between complete revolutions of said helical structure;

each of said helical structures having adaptive means for receiving data concerning a set of multiple diverse parameters used to characterize the complex entity which said helical structure represents, said data concerning said set of parameters being superimposed upon said adaptive means, said adaptive means comprising radially and sequentially disposed primary zones of substantially equal area and substantially similar shape within the helical structure, each of said primary zones being defined by first and second sequential radial lines between said inner and outer bounding cylinders on said helical structure, said inner and outer bounding cylinders, and an included angle between said radial lines, and each of said primary zones being allocated for superimposition of a representation of data thereon and relating to a single one of said parameters used to characterize said complex entities.

2. The system of claim 1 wherein each of said primary zones further includes a series of secondary zones, each of said secondary zones being defined by a pair of segments of said first and second radial lines of said primary zone, a pair of lines extending between said segments, and said included angle between the radial lines of said primary zone.

3. The system of claim 2 in which said pair of segments of said first and second radial lines of said primary zone, and said lines extending therebetween further constitute scale means for quantitative representation of said data.

4. The system of claim 3, wherein said representation of said data includes superimposing discrete shaded areas upon said secondary zones, said shaded areas extending over a portion of said primary zones corresponding to a graphical representation of a numerical value associated with said related parameter.

5. The system of claim 4, wherein said shaded areas are of progressively increased hue and density with increased radial disposition of said secondary zones from said inner bounding cylinder of said helical structures, whereby said shaded areas provide means for visual comparison of said represented data relating to the parameter to which said primary zone relates.

6. The system of claim 2, wherein said lines partially defining said secondary zones are straight lines and said inner and outer bounding cylinders are polygonal having a number of sidewalls equal to a quantity of primary zones included in a single rotation of said helical structure, whereby said secondary zones of each primary zone form a series of substantially trapezoidal areas within said primary zone, progressively increasing in size with increasing distance from said inner bounding cylinder.

7. The system of claim 2, wherein said lines partially defining said secondary zones are curved lines, whereby said secondary zones of each primary zone form a series of substantially annular sectors, progressively increasing in size with increasing distance from said inner bounding cylinder.

8. The system of claims 3, 4, 5, 6, or 7, wherein said scale means is a linear scale means for quantitative representation of said data.

9. The system of claims 3, 4, 5, 6, or 7, wherein said scale means is a logarithmic scale means for quantitative representation of said data.

10. The system of claims 3, 4, 5, 6, 7, 8, or 9, wherein said scale means for each primary zone is defined in the same units as the parameter to which said primary zone relates.

11. The system of claim 5, wherein said discrete shaded areas of said representation of data are in the form of a grey scale.

12. The system of claim 5, wherein said discrete shaded areas of said representation of data are in the form of a color scale.

13. The system of claims 1 or 12, wherein parameters naturally associated are allocated to a group of adjacent said primary zones.

14. The system of claim 13, wherein said parameters within any said group are allocated related colors.

15. A system for comparing a plurality of complex entities wherein a first set of data concerning a set of multiple diverse parameters is used to characterize a first complex entity and one or more additional sets of data concerning said set of parameters is used to characterize one or more additional complex entities, said system comprising:

a separate helical structure for representing each of said complex entities, said helical structure being defined by an outer bounding cylinder, an inner bounding cylinder coaxial with said outer bounding cylinder and a pitch between complete revolutions of said helical structure;

each of said helical structures having adaptive means for receiving data concerning a set of multiple diverse parameters used to characterize the complex entity which said helical structure represents, said data concerning said set of parameters being superimposed upon said adaptive means, said adaptive means comprising radially and sequentially disposed primary zones of substantially equal area and substantially similar shape within the helical structure, each of said primary zones being defined by first and second sequential radial lines between said inner and outer bounding cylinders on said helical structure, said first and second sequential radial lines each having an innermost end and an outermost end, an inner segment connecting said innermost ends of said radial lines, an outer segment connecting said outermost ends of said radial lines, an included angle between said radial lines, and each of said primary zones being allocated for superimposition of a representation of data thereon and relating to a single one of said parameters used to characterize said complex entities.

16. The system of claim 15, wherein each of said inner segments partially defining said primary zones is coplanar with a sidewall of a polygon, said polygon being coaxial with said inner bounding cylinder and having a number of sidewalls equal to a quantity of primary zones included in one revolution of said helical structure.

17. The system of claim 15, wherein each of said inner segments partially defining said primary zones is coextensive with a sidewall of said inner bounding cylinder.

18. The system of claim 17, wherein each of said outer segments partially defining said primary zones is coextensive with a sidewall of said outer bounding cylinder.

19. The system of claim 15, wherein each of said first and second sequential radial lines of said primary zone further has a plurality of equidistantly-spaced points thereon, each of said points defining an endpoint of a secondary zone segment and each of said primary zones further including a series of secondary zones, each of said secondary zones being defined by a pair of segments of said first and second radial lines of said primary zone, a pair of said secondary zone segments extending between a pair of said endpoints along said first radial line and a corresponding pair of said endpoints along said second radial line, and said included angle between the radial lines of said primary zone.

20. The system of claim 19, in which said sequential radial lines, said equidistantly-spaced points, and said pairs of secondary zone segments constitute scale means for quantitative representation of said data.

21. The system of claim 20, said adaptive means further comprising means for indicating on each primary zone a maximum data value of the parameter to which the primary zone is related, said maximum data value corresponding to a quantitative measure of said parameter in said complex entity.

22. The system of claim 21, wherein said means for indicating a maximum data value comprises a data value segment extending between a pair of data points on said first and second sequential radial lines, said data points and said data value segment positioned on said scale means at a location corresponding to said quantitative measure of said parameter in said complex entity, whereby when said data value segment is between a pair of said secondary zone segments, a partial zone is created within a secondary zone.

23. The system of claim 22, wherein said representation of said data includes superimposing discrete shaded areas upon said secondary zones, said shaded areas extending over a portion of said primary zones corresponding to a graphical representation of said quantitative value of said related parameter, and terminating at said data value segment.

24. The system of claim 23, wherein said shaded areas are of progressively increased hue and density with increased radial disposition of said secondary zones from said inner bounding cylinder of said helical structures, whereby said shaded areas provide means for visual comparison of said represented data relating to the parameter to which said primary zone relates.

25. The system of claim 24, and further comprising electronic means for generating said helical structures in a virtual format on a computer screen.

26. The system of claim 25, wherein said electronic means includes means for manipulating said helical structures, said manipulating including one or more of the group of:

duplicating one or more of said helical structures;

adjusting the size of one or more of said helical structures;

adjusting the scale of one or more parameters of said helical structures;

adjusting the orientation of said helical structures for viewing different parts thereof;

separating sections of said helical structures, each of said sections being one of said complete revolutions of said helical structures, in order to compare one revolution of a helical structure corresponding to a first complex entity with a corresponding revolution of a second helical structure corresponding to a second complex entity;

superimposing a helical structure representing one complex entity onto a second helical structure representing another complex entity;

superimposing separate sections of a helical structure representing one complex entity onto corresponding sections of a second helical structure representing another complex entity, each of said sections being one of said complete revolutions of said helical structures;

and selectively hiding said sequential radial lines, said data value lines, and said secondary zone segments.

27. The system of claim 23, wherein one of said separate helical structures further comprises a tolerance zone in each of said primary zones, said tolerance zone being defined by:

a low tolerance limit segment connecting said first and second sequential radial lines of the separate helical structure, corresponding to a lowest allowable value for the corresponding parameter represented by said primary zone;

a high tolerance limit segment connecting said first and second sequential radial lines of the separate helical structure at a greater distance from said inner bounding cylinder than said low tolerance limit segment and corresponding to a highest allowable value for said parameter; and a pair of segments of said first and second sequential radial lines extending between said low and high tolerance limit segments, whereby when said helical structure corresponding to a first complex entity is superimposed on said separate helical structure a user can observe whether said first complex entity satisfies a set of tolerances for all of the represented parameters by determining whether said discrete shaded areas of each of the primary zones of said helical structure corresponding to a first complex entity terminates within said tolerance zone of each primary zone of said separate helical structure.

28. The system of claims 15, and further comprising means for communicating one or more of said sets of data concerning said set of multiple diverse parameters between a plurality of locations.

29. The system of claim 28, wherein said communicating means comprises electronic communication means selected from a group including telephones, facsimile machines, computers provided with modems, and satellite communication.

30. The system of claim 15, wherein said solid helical structures are provided with a label area for each of said radially disposed primary zones.

31. The system of claim 15, wherein the number of primary zones in each of said revolution of said helical structures is in the range of 10 to 25.

32. The system of claim 15, wherein said outer bounding cylinder has a radius of about 75 mm.

33. The system of claim 32, wherein the ratio between said pitch of one of the helical structures and said radius of the outer bounding cylinder is about 0.67:1.0.

34. A method for use by one or more parties for comparing a plurality of complex entities wherein a first set of data concerning a set of multiple diverse parameters is used to characterize a first complex entity and one or more additional sets of data concerning said set of parameters is used to characterize one or more additional complex entities, comprising the steps of:

generating a separate helical structure representing each of said complex entities, each of said helical structures being defined by an outer bounding cylinder, an inner bounding cylinder coaxial with said outer bounding cylinder and a pitch between complete revolutions of said helical structure, each of said helical structures having adaptive means for receiving data concerning a set of multiple diverse parameters used to characterize the complex entity which said helical structure represents, said data concerning said set of parameters being superimposed upon said adaptive means, said adaptive means comprising radially and sequentially disposed primary zones of substantially equal area and substantially similar shape within the helical structure, each of said primary zones being defined by first and second sequential radial lines between said inner and outer bounding cylinders on said helical structure, said inner and outer bounding cylinders, and an included angle between said radial lines, and each of said primary zones being allocated for superimposition of a representation of data thereon and relating to a single one of said parameters used to characterize said complex entities and including a series of secondary zones within each primary zone, each of said secondary zones being defined by a pair of segments of said first and second radial lines of said primary zone, a pair of lines extending between said segments, and said included angle between the radial lines of said primary zone;

assigning a quantitative scale to each of said primary zones of the helical structures, with said lines partially defining said secondary zones constituting scale means of said quantitative scale; and superimposing one or more discrete shaded entities upon said secondary zones of each primary zone, said shaded entities progressively increasing in hue and density with increased radial disposition of said secondary zone from the axis of said bounding cylinders of said helical structure and extending over a number of secondary zones in the associated primary zone to correspond to a quantitative representation of a measurement of a parameter in the complex entity represented by said helical structure.

35. The method of claim 34, further comprising the step of:

comparing said discrete shaded entities in each parameter of one of said helical structures with corresponding discrete shaded entities in each parameter of another of said helical structures representing a separate complex entity.

36. The method of claim 34, further comprising the steps of:

manipulating two of said helical structures by separating each of said structures into a plurality of sections, each of said sections defined by one complete revolution of one of said helical structures;

placing each of said sections in a substantially similar orientation relative to one another; and comparing said discrete shaded entities in each parameter of said superimposed sections.

37. The method of claim 36, further comprising the step of comparing said sections in their entirety.

38. The method of claim 34, further comprising the steps of:

manipulating two of said helical structures by separating each of said structures into a plurality of sections, each of said sections defined by at least one of said primary zones and by no more than one complete revolution of one of said helical structures;

superimposing one of said sections of a first helical structure onto a corresponding section of a second helical structure; and comparing said discrete shaded entities in each parameter of said super imposed sections.

* * * * *